United States Patent
List et al.

(10) Patent No.: US 7,811,236 B2
(45) Date of Patent: Oct. 12, 2010

(54) PUNCTURING SYSTEM FOR COLLECTING BODY FLUID SAMPLE

(75) Inventors: Hans List, Hesseneck-Kailbach (DE); Hans-Peter Haar, Wiesloch (DE); George Bevan Kirby Meacham, Shaker Heights, OH (US); Michael Eusemann, Reinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 72 days.

(21) Appl. No.: 12/122,908

(22) Filed: May 19, 2008

(65) Prior Publication Data
US 2008/0262388 A1    Oct. 23, 2008

Related U.S. Application Data

(63) Continuation of application No. PCT/EP2006/012016, filed on Dec. 13, 2006.

(30) Foreign Application Priority Data
Dec. 15, 2005    (EP) .................................. 05027428

(51) Int. Cl.
*A61B 5/00* (2006.01)
*A61B 5/15* (2006.01)
*A61B 5/157* (2006.01)
*A61B 17/32* (2006.01)

(52) U.S. Cl. ................... 600/583; 600/573; 606/181

(58) Field of Classification Search ................ 600/583, 600/573, 576, 584; 606/181, 182
See application file for complete search history.

(56) References Cited

U.S. PATENT DOCUMENTS

| 4,637,403 | A | 1/1987 | Garcia et al. |
|---|---|---|---|
| 6,589,260 | B1 | 7/2003 | Schmelzeisen-Redeker et al. |
| 7,288,073 | B2 | 10/2007 | Effenhauser et al. |
| 2002/0103499 | A1 | 8/2002 | Perez et al. |
| 2003/0018282 | A1 | 1/2003 | Effenhauser et al. |
| 2003/0083685 | A1 | 5/2003 | Freeman et al. |
| 2004/0059256 | A1 | 3/2004 | Perez |
| 2008/0082023 | A1 | 4/2008 | Deck et al. |
| 2008/0108910 | A1 | 5/2008 | Hein et al. |

FOREIGN PATENT DOCUMENTS

| WO | WO 02/100275 | 12/2002 |
|---|---|---|
| WO | WO 2004/041087 | 5/2004 |
| WO | WO 2005/001418 A2 | 1/2005 |
| WO | WO 2005/001418 A3 | 1/2005 |
| WO | WO 2007/025635 | 3/2007 |

*Primary Examiner*—Max Hindenburg
*Assistant Examiner*—Emily M Lloyd
(74) *Attorney, Agent, or Firm*—Baker & Daniels LLP

(57) ABSTRACT

A microsampler puncturing system for collecting a body fluid from a body part is described, comprising a sample collection unit having a piercing element, and a puncturing instrument having a drive, by which a sample collection unit is movable on a movement path for piercing the piercing element into the skin of the body part and withdrawing it in a piercing and retraction movement, a setting device for setting the puncturing depth of the piercing wound to be generated, and a control device for controlling the piercing and retraction movement having the following sequentially executed movement phases: a forward phase, a retraction phase, and a collecting phase (S). The setting device is settable independently of the chronological mean <dr> of the defined residual puncturing depth (dr), with reference to the collecting phase.

25 Claims, 14 Drawing Sheets

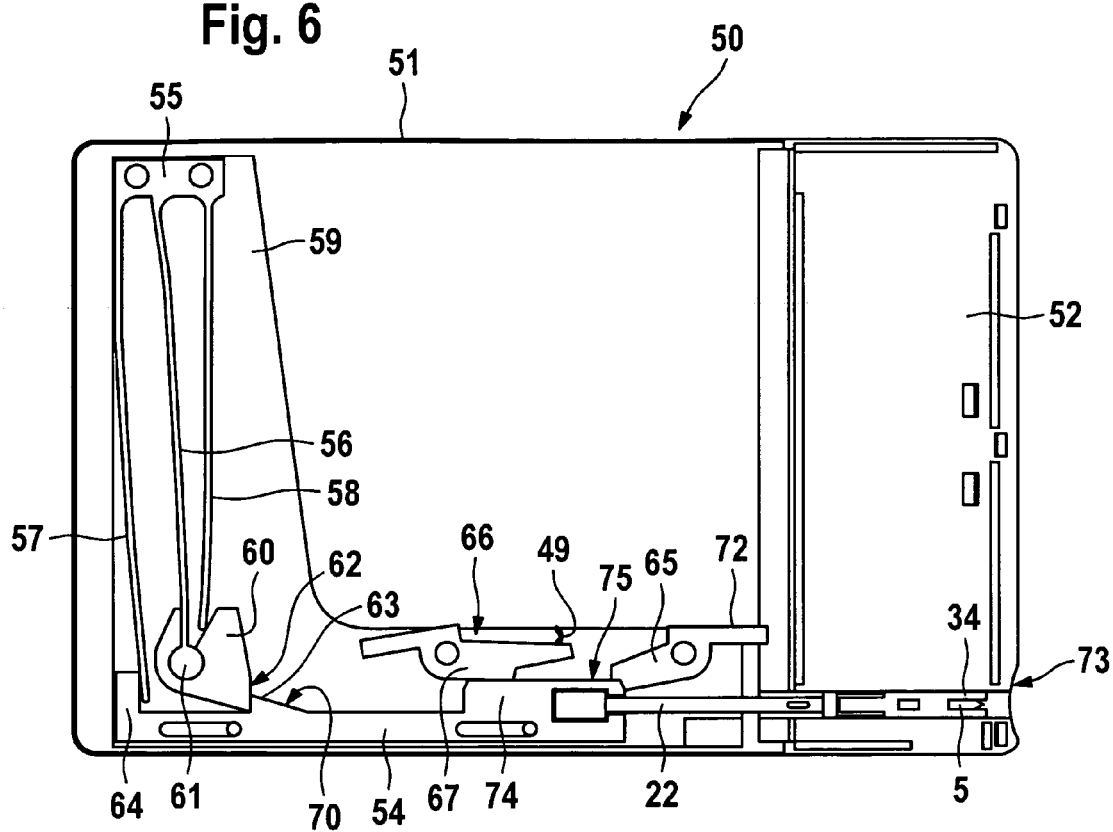
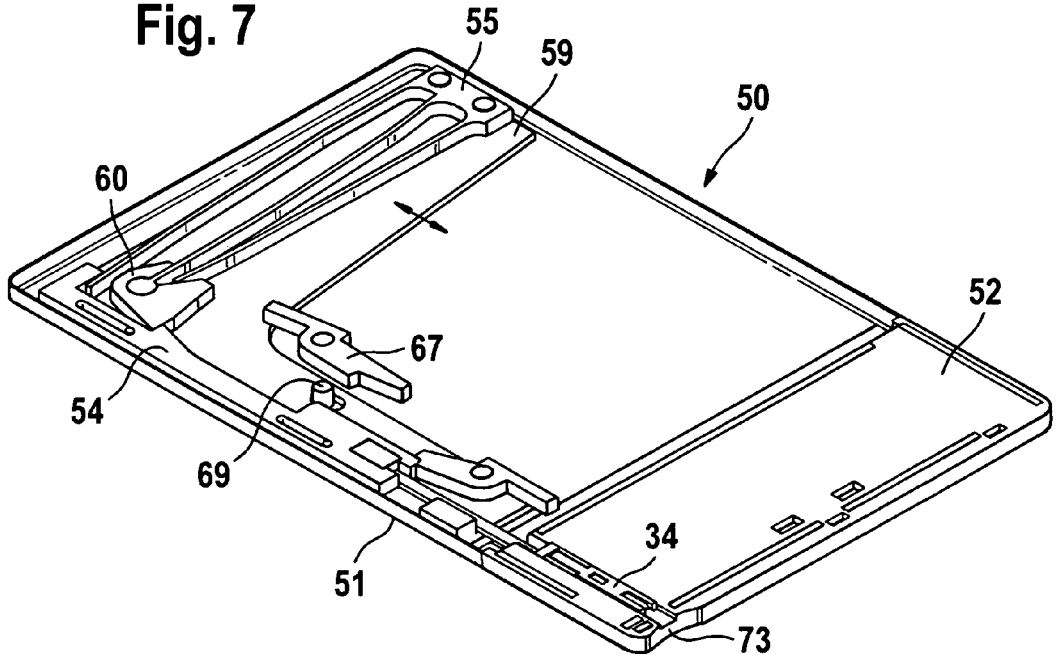

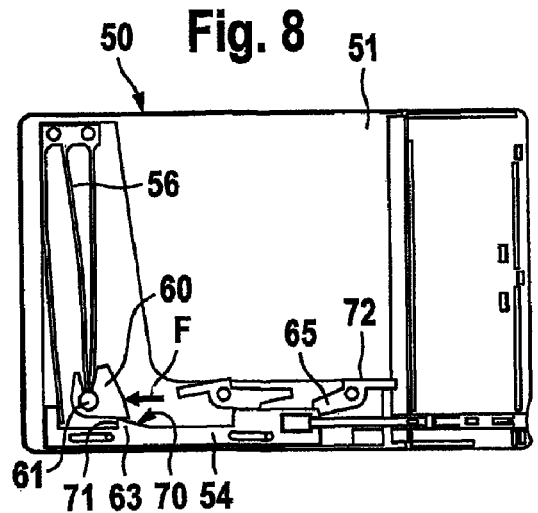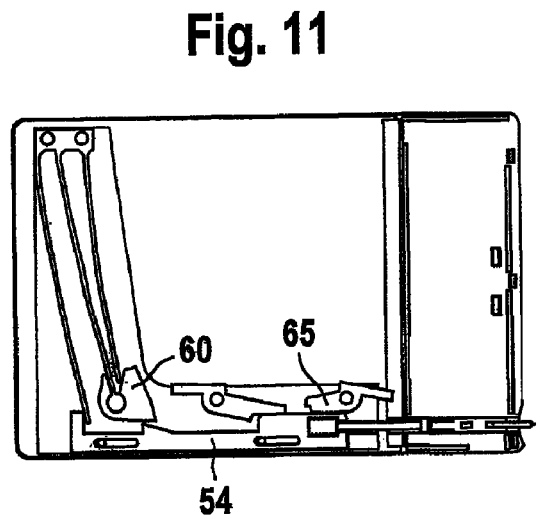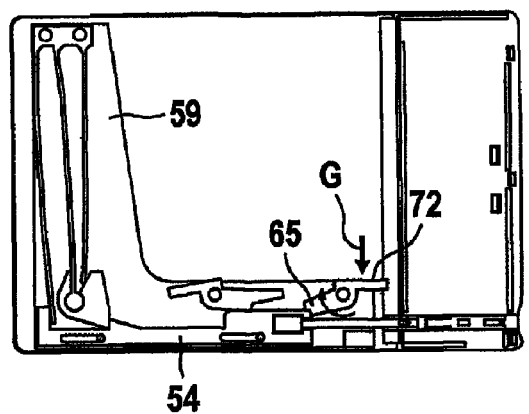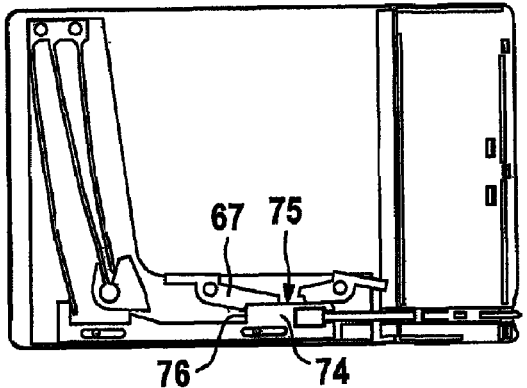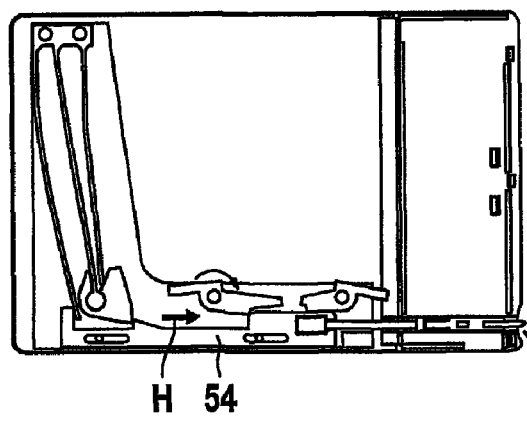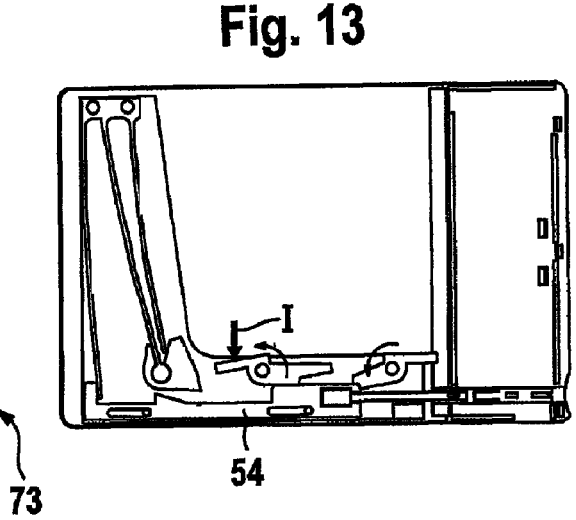

PUNCTURING SYSTEM FOR COLLECTING BODY FLUID SAMPLE

RELATED APPLICATIONS

This application is a continuation of PCT/EP06/012016, filed Dec. 13, 2006, the entire disclosure of which is expressly incorporated herein by reference.

FIELD OF THE INVENTION

The invention relates to a microsampler puncturing system for collecting a body fluid sample from a body part. Puncturing systems comprise a sample collection unit having a piercing element and a puncturing instrument having a drive, by which a sample collection unit is movable on a movement path for piercing the piercing element into the skin of a body part and retract it again by a piercing and retraction movement.

BACKGROUND AND SUMMARY OF THE INVENTION

The sample collection unit of a microsampler puncturing system is not only used for generating a piercing wound, but rather also for collecting a small sample of body fluid. The collected sample volume is typically at most a few microliters. Therefore puncturing systems of this type are referred to as "microsampler puncturing systems". A sample collection unit for a microsampler puncturing system is known from WO 03/009759 A1. For sample collection, the piercing element, after a first piercing, by which a piercing channel is generated, may be pierced again at a lesser depth into the piercing channel in a second piercing (European Patent Application 05019190.7). The piercing element remains in the piercing channel during a collecting phase after the second piercing, so that body fluid may be withdrawn through the capillary channel. A further possibility for sample collection is to only partially retract the piercing element after the piercing for generating the piercing channel, so that it remains at a lesser depth in the piercing channel during a collecting phase (WO 02/100275).

Due to the automatic sample collection, microsampler puncturing systems are a great convenience for diabetics, who must check their blood sugar level a plurality of times per day. An object of the invention is to indicate a way in which microsampler puncturing systems may be improved further with respect to sample acquisition and pain perception.

This object is achieved by a microsampler puncturing system for collecting a body fluid sample from a body part, comprising a sample collection unit having a piercing element, and a puncturing instrument having a drive, by which the sample collection unit is movable on a movement path for piercing the piercing element into the skin of the body part and retract it again by a piercing and retraction movement, a setting device for setting a defined puncturing depth (dm) of the piercing wound to be generated, and a control device for controlling the piercing and retraction movement having the following sequentially executed movement phases a forward phase, in which the piercing element is moved in a puncturing direction and pierced to a defined puncturing depth, a retraction phase, in which the piercing element is partially retracted by a retraction distance and decelerated toward the end of the retraction phase (R1), so that it projects into the skin at a defined residual puncturing depth, and a collecting phase, in which the piercing element projects into the skin at the defined residual puncturing depth and a body fluid sample is withdrawn by the sample acquisition unit, the setting device being adapted for setting the puncturing depth independently of the mean value, with reference to the collecting phase, of the defined residual puncturing depth.

The residual puncturing depth does not have to be constant during the collecting phase. Rather, a slow movement during the collecting phase, preferably at a velocity of at most 0.3 mm/seconds, more preferably at most 0.1 mm/seconds, is possible and in many applications even advantageous. In particular, this is a slow retraction movement (opposite to the puncturing direction). In order to take this into consideration in the definition of the invention, reference is not made to the residual puncturing depth dr during the collecting phase, but rather to its mean value <dr>. The mean value <dr> of the residual puncturing depth dr is understood as the quotient of the time integral of the puncturing depth d(t) from the beginning of the collecting phase at the time t1 up to the end of the collecting phase at the time t2 and the duration of the collecting phase (t2 minus t1):

$$<dr> = \frac{\int_{t_1}^{t_2} d(t)dt}{t_2 - t_1}$$

In general, the beginning and end of the collecting phase, i.e., the times t1 and t2 are defined in that the withdrawal of the body fluid, after the deceleration of the piercing element, starts and ends, respectively.

The piercing element is preferably stopped at the end of the retraction phase, so that the residual puncturing depth is constant during the collecting phase. In this case, the mean value <dr> corresponds to the constant value of the residual puncturing depth.

In the context of the invention it has been established that the residual puncturing depth of the piercing element during the collecting phase is very important for the sample acquisition and the pain perception. In particular, it is important for low-pain and efficient sample collection that a defined value of the puncturing depth can be set independently of the predetermined (defined) value of the residual puncturing depth. In other words, the value of the defined residual puncturing depth should not be adjusted automatically by the same amount when the setting of the defined puncturing depth is changed. In this respect, the invention differs significantly from previously known microsampler puncturing systems:

Typically, in known microsampler puncturing systems, the residual puncturing depth was changed congruently (i.e., in the same direction and by the same absolute value) when the setting of the puncturing depth was changed. This corresponds to the prevailing opinion that, if a person requires a greater puncturing depth for obtaining blood (for example, a worker having thick callous), the residual puncturing depth must also be correspondingly greater.

In exceptional cases, only the puncturing depth was set in a defined manner, while with respect to the residual puncturing depth, the design was not adapted to ensure a predetermined (defined) depth value. For example, in US 2004/0059256, a puncturing system is described in which the residual puncturing depth is a function of the friction of several components and of the orientation of the puncturing instrument during use. This corresponds to the opinion that it is not the residual puncturing depth, but rather the puncturing depth which is important with respect to low-pain acquisition of a sufficiently large blood droplet.

Surprisingly, setting the residual puncturing depth to adapt to the requirements of a specific patient is not absolutely necessary, rather a defined, non-settable residual puncturing depth may be used independently of the patient, although thickness and strength of the uppermost skin layer differ substantially from patient to patient. According to a preferred embodiment, the residual puncturing depth is also settable—independently of the puncturing depth.

A further aspect of the invention which also has independent significance, relates to a puncturing instrument, in particular for a puncturing system according to any one of the preceding claims, comprising a lancet holder for receiving a sample collection unit and a drive for accelerating the lancet holder for a piercing and retraction movement, characterized in that the lancet holder is coupled to a damping mechanism to damp the deceleration of the lancet holder toward the end of a retraction movement.

By means of a damping mechanism according to the invention, the drive movement may be slowly stopped at the end of a retraction movement, so that painful oscillations of the piercing element may be reliably avoided. This is especially important if, at the time of stopping the movement, the piercing element projects by a residual puncturing depth into the skin of the patient.

BRIEF DESCRIPTION OF THE DRAWINGS

The invention is explained in greater detail hereafter on the basis of exemplary embodiments with reference to the attached drawings. The special features shown therein may be used individually or in combination to provide preferred embodiments. In the Figures:

FIG. 6 shows a further example of a puncturing instrument according to the invention in a side view;

FIG. 7 shows the example shown in FIG. 6 in a perspective illustration;

FIG. 8 shows the example shown in FIG. 6 during tensioning of the drive spring;

FIG. 9 shows the example shown in FIG. 6 in the tensioned state;

FIG. 10 shows the example shown in FIG. 6 at the beginning of the forward phase;

FIG. 11 shows the example shown in FIG. 6 at the end of the forward phase;

FIG. 12 shows the example shown in FIG. 6 during the collecting phase; and

FIG. 13 shows the example shown in FIG. 6 during the final retraction phase after the end of the collecting phase.

DETAILED DESCRIPTION OF EMBODIMENTS OF THE INVENTION

Figure 1:
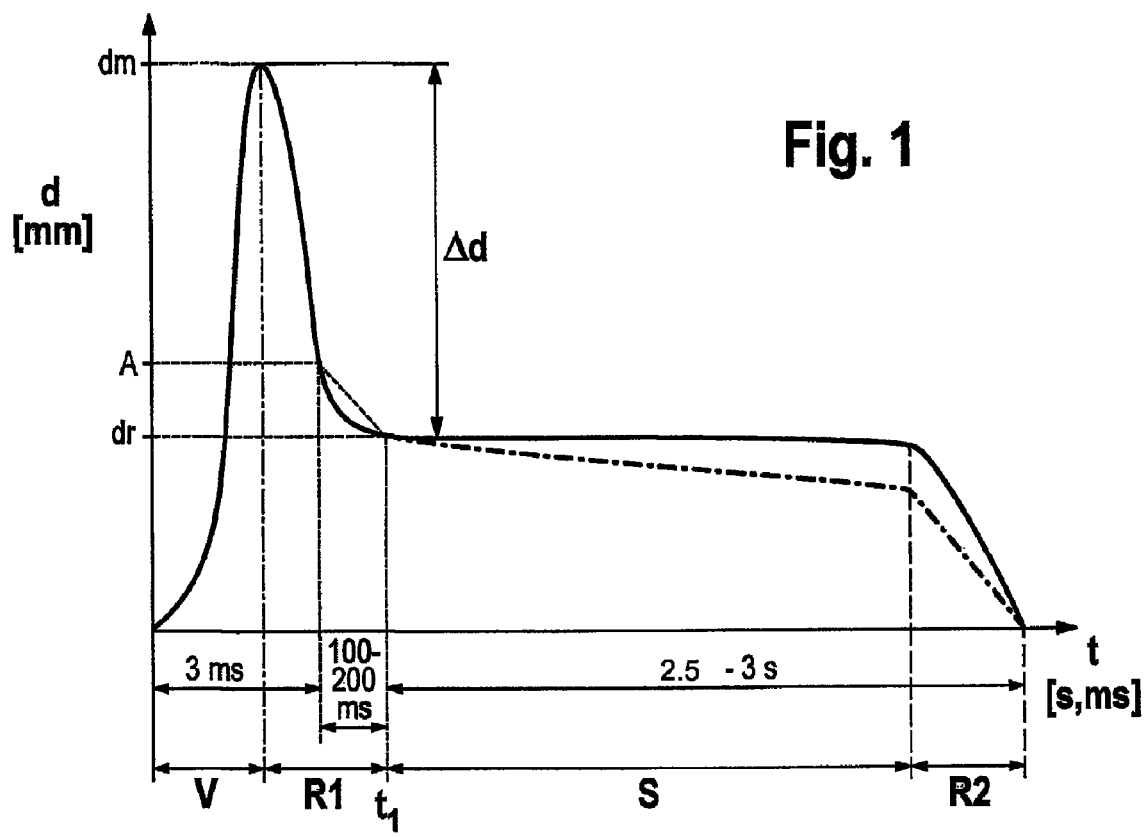
FIG. 1 shows an example of the curve of the puncturing depth over time.

The time curve of the puncturing depth d of a piercing element during the forward phase V, the retraction phase R1, and the collecting phase S is shown in FIG. 1. The zero line corresponds to the position of the skin surface. The division of the time axis in FIG. 1 is different in different sections thereof, because the forward and retraction phases are executed within a few milliseconds, while the duration of the collecting phase is to be measured in the scale of seconds.

At the end of the forward phase V, the piercing element reaches a maximal puncturing depth dm which is typically 0.8 mm to 2.3 mm, depending on the setting. The forward phase V is followed by a retraction phase R1 in which the piercing element is partially retracted by a retraction distance Δd and decelerated toward the end of the retraction phase, so that it projects into the skin at a residual puncturing depth dr of 0.5 mm, for example. The residual puncturing depth is predetermined (defined) by the device design and is thus reproducible.

For a low-pain piercing, it is essential that the piercing element is pierced very rapidly during the forward phase V and is retracted again very rapidly on at least a part of the retraction distance Δd. Preferably velocities of at least 200 mm/second, especially preferably at least 500 mm/second are achieved. On a further part of the retraction distance Δd, the piercing element is decelerated for the collecting phase, so that the last remainder of the retraction distance Δd is passed substantially more slowly. In the curve shown in FIG. 1, the forward phase V and the first part of the retraction distance are passed in approximately 3 ms. The remaining retraction phase (beginning from the puncturing depth A) lasts approximately 100 ms to 200 ms.

At the end of the retraction phase R1, the piercing element is stopped at a constant residual puncturing depth dr for the collecting phase S. As already noted, it is possible or even advantageous in many applications if a slow retraction movement (opposite to the puncturing direction) takes place during the collecting phase. This possibility is shown in FIG. 1 by a dot-dash line. In any case, the residual puncturing depth dr has a defined value during the collecting phase. Accordingly, its mean value <dr>, with reference to the collecting phase, also has a defined value.

During the collecting phase a body fluid sample, typically blood or interstitial liquid, is withdrawn through a capillary channel of the sample collection unit. The capillary channel is preferably laterally open along at least a part of its length (US 2003/0018282A1). The collecting phase should be as short as possible. It typically lasts less than one second. After the collecting phase, the piercing element is accelerated again and completely withdrawn from the skin in a second retraction phase R2.

Figure 2:
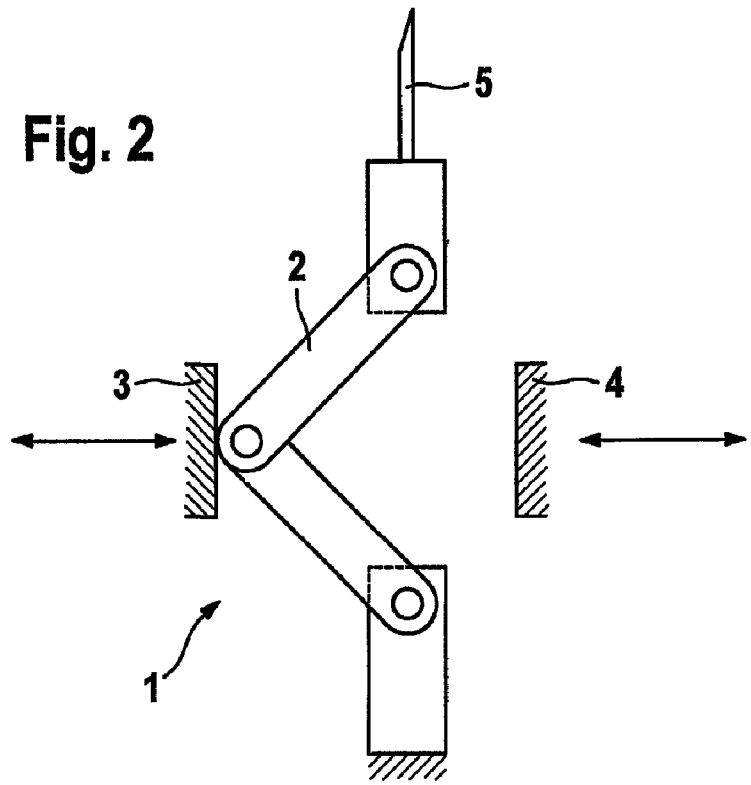
FIG. 2 shows a schematic sketch of an example of a puncturing instrument according to the invention.

An example of a design, by which the piercing profile shown in FIG. 1 may be implemented, is shown in FIG. 2. The control device 1 comprises a pivot element 2 in the form of a toggle joint located between two lateral stops 3, 4. To cause an insertion and retraction movement of the piercing element 5, the toggle joint 2 passes, under the effect of a drive force, from the bent starting position shown in FIG. 2 into a stretched intermediate position and further into a reversed bent final position, in which it presses against the end stop 4. The piercing element 5 reaches its maximal puncturing depth in the stretched intermediate position (not shown).

The position to which the piercing element 5 is retracted during the retraction phase may be set by the position of the end stop 4. The more the end stop 4 is shifted to the right in FIG. 2, the larger is the retraction distance Δd during the retraction phase R1. The end stop 4 thus forms, in the exemplary embodiment shown, a retraction stop, by which the piercing element 5 is stopped in a defined position, which position corresponds to the position of the end stop at the end of retraction phase R1. After the end of the collecting phase, the end stop 4 may be moved into a final position (i.e., entirely to the right in the configuration shown in FIG. 2), so that the piercing element 5 is withdrawn completely from the skin in the retraction phase R2.

The drive force for moving the toggle joint 2 is generated by a drive spring (not shown). During the piercing movement, the toggle joint is moved by the spring force from the starting stop 3 to the end stop 4.

The depth setting is performed in two steps: the starting stop 3 is set in such a manner that the maximal movement range of the piercing element 5 corresponds to the maximal puncturing depth. The end stop 4 is set preferably simultaneously and coupled thereto, in such a manner, that the return distance of the piercing element is shorter by the residual puncturing depth.

According to an advantageous design, in this embodiment, and also in general in the present invention, the position of the skin surface may be detected before the triggering of a piercing movement. Thereafter the piercing movement may be adjusted to the detected position. It is thereby possible to ensure a reproducible maximal puncturing depth even if the skin bulges into the front housing opening of the puncturing instrument (not shown here) and if this bulging varies when the puncturing instrument is pressed against the skin because of its elasticity ("Z-variance"). Such a prior detection of the skin surface may be implemented, for example, by moving the mechanism shown in FIG. 2 forward along a linear guide (in the puncturing direction) until the tip of the piercing element 5 contacts the skin surface. This contact can be electronically detected. Such a design is explained in connection with FIGS. 29 through 31. The same drive which is used for this prior detection may also be used for withdrawing the needle element in the second retraction phase R2.

In order to allow simultaneous setting of the starting stop 3 and the end stop 4, a planar thread may be used, for example, as is typical in jaw chucks of lathes. In this context it must be taken into account that a nonlinear relationship exists between the displacement path of the stops 3, 4 and the puncturing depth. To make the setting easier, this nonlinearity may be compensated for by a suitable cam shape or control link, for example. The position of the stops 3, 4 may be set manually or processor-controlled using a suitable electric motor, which may also be used for tensioning the drive spring, for example.

Figure 3:
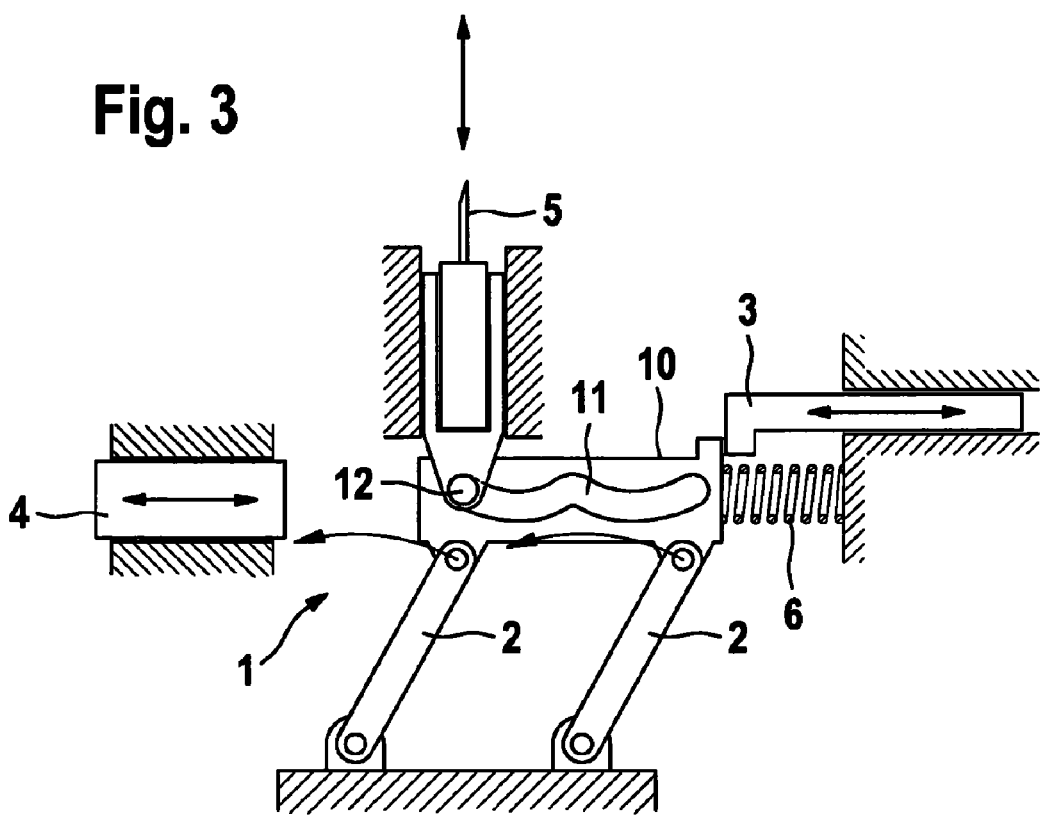
FIG. 3 shows a schematic sketch of a further example.

A further example of a design, by which the piercing profile shown in FIG. 1 may be implemented, is shown in FIG. 3. The control device 1 comprises a pivot element 2 in the form of a parallelogram guide located between two lateral stops 3, 4. To cause an insertion and retraction movement of the piercing element 5, the parallelogram guide 2 passes under the effect of the drive force generated by a drive spring 6 from the starting position shown in FIG. 3 into a final position, in which it presses against the end stop 4.

The parallelogram guide 2 comprises a control element 10 having a control curve 11. A control curve traveler 12 travels along the control curve 11 during a piercing and retraction movement, so that the pivoting movement of the parallelogram guide 2 is converted into a linear piercing and retraction movement of the piercing element 5. In the exemplary embodiment shown, the control curve 11 is implemented as a groove, in which a control curve traveler 12 implemented as a pin engages.

As in the exemplary embodiment described on the basis of FIG. 2, the position of the stops 3 and 4 may be set to define how far the piercing element 5 is moved forward and backward. A linear relationship between the position of the end stops 3 and 4 and the piercing stroke may be achieved by the shape of the control curve 11. This makes setting of the puncturing depth easier.

In the exemplary embodiment shown, the control curve traveler 12 does not travel along the entire control curve 11, but rather only an active section of the control curve 11 during the forward phase V and the retraction phase R1. The beginning and end of the active section are predefined by the positions of the stops 3 and 4. The function essentially corresponds to the embodiment shown in FIG. 2.

Figure 4:
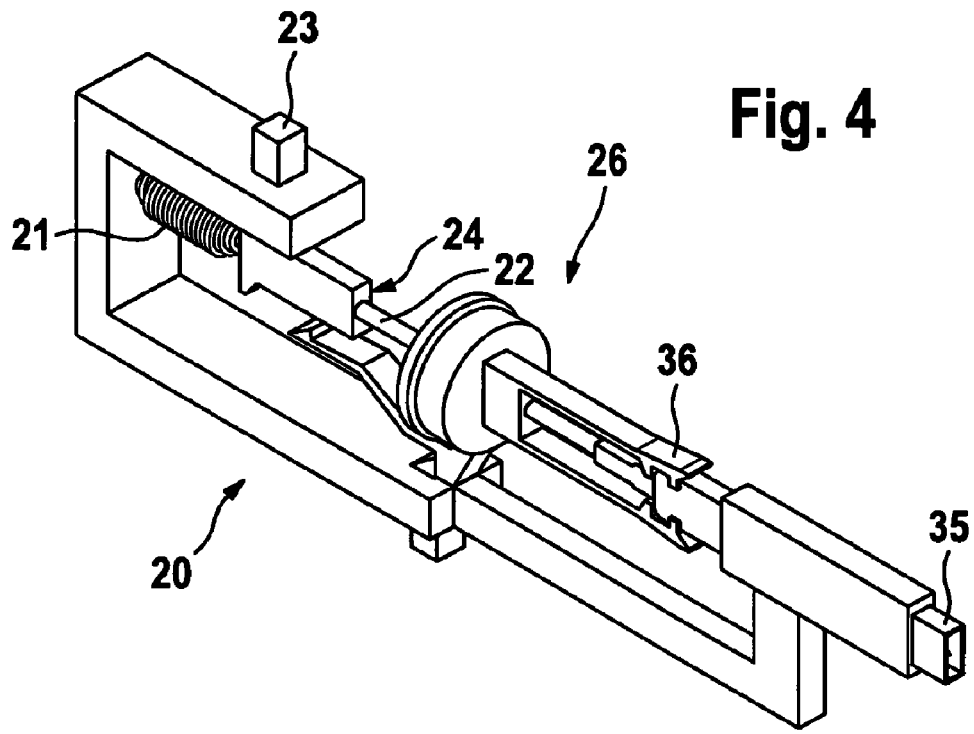
FIG. 4 shows a further exemplary embodiment of a puncturing instrument according to the invention without housing in a side view.
Figure 5:
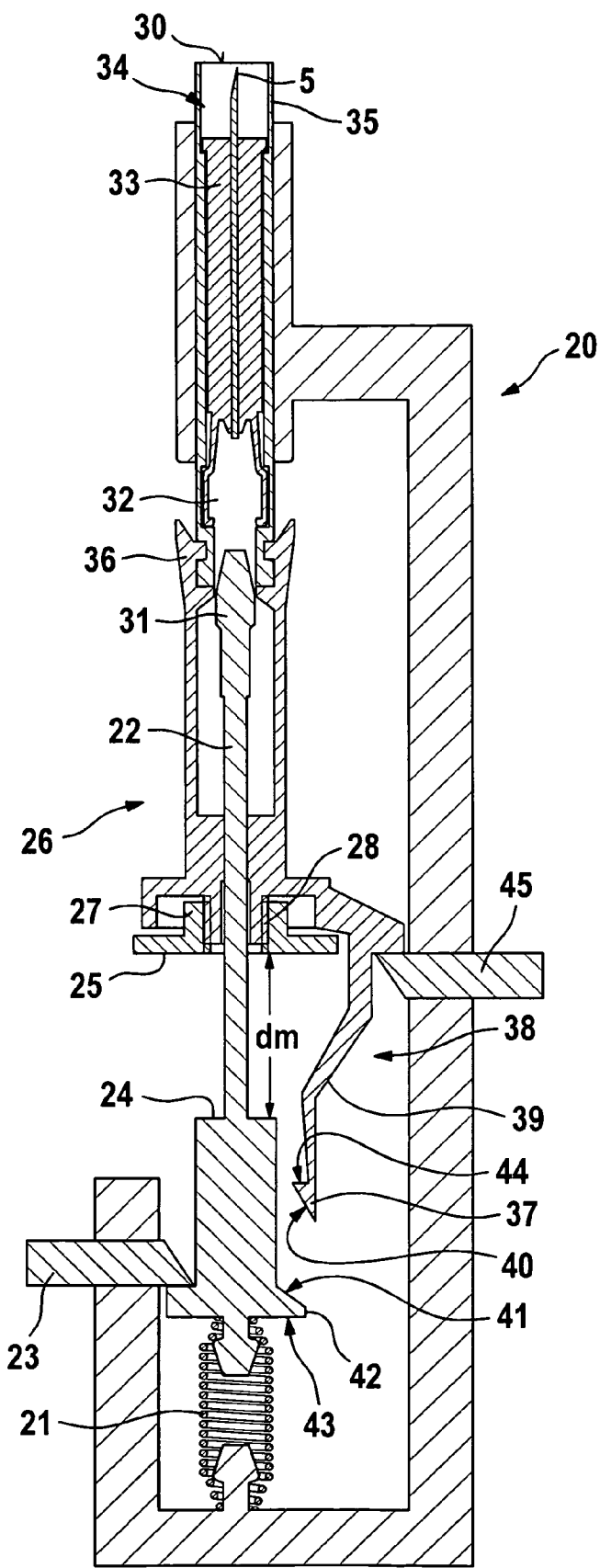
FIG. 5 shows the exemplary embodiment shown in FIG. 4 in a cross-sectional view.

FIGS. 4 and 5 show a further example of a puncturing instrument 20, by which the puncturing profile shown in FIG. 1 may be implemented. For simplification, only the essential parts of the puncturing instrument 20 are shown, without a complete instrument housing.

The puncturing instrument 20 has a spring drive having a drive spring 21. The drive spring 21 is a coiled spring, which is shown in the compressed state in FIGS. 4 and 5. The drive spring 21 is coupled to a pushrod 22, which is accelerated by the drive spring 21 in the puncturing direction as soon as a trigger element 23 is actuated. The trigger element 23 is a bolt which locks the pushrod 22 in the holding position shown. For triggering, the bolt is retracted in such a manner that the pushrod 22 may be accelerated by the drive spring 21 in the puncturing direction.

During the forward phase V, the pushrod 22 moves until it impacts, by means of a stop 24 provided on the pushrod 22, against a stop 25 of a setting device 26 at the end of the forward phase V. The stop 25 is formed by the head of a set screw 27, whose thread 28 runs parallel to the puncturing direction. The longitudinal position of the stop 25 in relation to a reference surface 30 pressing against the skin may be set by rotating the set screw 27. The puncturing depth of a piercing wound generated during piercing is predefined by the longitudinal position of the stop 25 and a corresponding longitudinal position of the reference surface 30 in relation to the longitudinal position of the tip of the piercing element 5. "Longitudinal position" refers in each case to the position in the direction in which the puncturing movement is performed.

Pushrod 22 has a head 31 which penetrates during the piercing movement into a matching coupling recess 32 of a lancet body 33 and is coupled in a fixed manner to the lancet 34. The lancet 34 shown in FIGS. 4 and 5 comprises a piercing element 5, which is embedded in a lancet body 33 made of plastic. The piercing element 5 has a capillary channel, so that body fluid may be withdrawn, using the lancet 34 as the sample collection unit during a collecting phase S. The lancet 34 is inserted together with a sleeve-shaped puncturing depth reference element 35 into the puncturing instrument 20. The front end of the puncturing depth reference element 35 contacts the skin surface during piercing and thereby forms a precise reference point for defining the puncturing depth.

To this end, exact longitudinal positioning of the reference element 35 in relation to the setting device 26 is necessary. In the case shown this is achieved by engaging of the puncturing depth reference element 35 with catch elements 36 of the setting device 26 upon correct positioning. In the exemplary embodiment shown, the reference element 35 has a groove at its rear end for this purpose, in which catch elements 36, implemented as catch hooks, engage.

When the stop 24 of the pushrod 22 contacts the stop 25 of the setting device 26 at the end of the forward phase V, the drive spring 21 is stretched, so that the pushrod 22 is retracted again by the drive spring 21 during the retraction phase R1. The spring force of the drive spring 21 is thus used both for accelerating the pushrod 22 during the forward phase V and also for accelerating the pushrod 22 in the reverse direction during the retraction phase R1.

At the end of the retraction phase R1, the pushrod 22 and thus also the lancet 34, having the piercing element 5 engaged therewith, are stopped by an abutting element 37 of a retraction stop 38. The residual puncturing depth dr is defined (at a given position of the reference element 35) by the longitudinal position of the retraction stop 38 in the puncturing direction. Any element by which the retraction movement of the piercing element 5 may be stopped in a defined longitudinal position is basically suitable as retraction stop.

In the embodiment shown, the retraction stop 38 comprises a spring element 39 in the form of an elastic arm, which carries the abutting element 37 in the form of a pawl at its free end. The pawl 37 has a beveled sliding face 40, on which a sliding face 41 of a catch projection 42 located on the pushrod 22 slides past during the forward phase V. The spring arm 39 of the retraction stop 38 yields upon this sliding passing during the forward phase V.

As soon as the catch projection 42 has passed the abutting element 37, it returns back into its original position because of the spring force applied by the elastic arm 39. In this original position it stops the pushrod 22 at the end of the retraction phase, a stop 43 of the catch projection 42 of the pushrod 22 abutting against a corresponding stop 44 of the abutting element 37.

In the exemplary embodiment shown, the retraction stop 38 is movable in relation to the device housing (not shown) and is fixed during the collecting phase S by a blocking bolt 45. At the end of the collecting phase, the blocking bolt 45 is retracted from the engagement position shown in FIG. 5 into a retraction position, so that the retraction stop 38 is retracted by the drive spring 21 together with the pushrod 22. The second retraction phase R2 is thus initiated by retracting the blocking bolt 45.

As already noted, the head of the pushrod 31 engages in a formfitting manner with the lancet 34, so that not only pushing forces, but rather also traction forces may be transmitted to the lancet 34 via the pushrod 22. In the exemplary embodiment shown, the retraction stop 38 is fixedly connected to the catch elements 36 of the setting device 26, with which the lancet sleeve 35 is engaged. A one-piece embodiment of the retraction stop 38 with the catch elements 36 as an injection-molded part is especially favorable. In this manner, the puncturing depth reference element 35 is also retracted during the further retraction phase R2 together with the retraction stop 38 and the pushrod 22.

The exit of body fluid from a piercing wound may be prevented by the contact pressure of the reference element 35. On the other hand, a strong contact pressure during piercing may contribute to a reduced pain sensation. An important special feature of the described exemplary embodiment is therefore that the reference element 35 is advanced together with the lancet at the end of the forward phase. If the reference element 35 is applied to the skin surface of the user before triggering the piercing or if it is moved in the direction toward the skin surface during the forward phase, the contact pressure during piercing is increased thereby. The puncturing depth is defined by the distance by which the piercing element 5 projects beyond the reference surface 30, by which the reference element 35 presses against the skin surface, at the end of the forward phase. During the retraction phase, the reference element 35 and the piercing element 5 are retracted, so that the contact pressure is reduced and the piercing element projects into the skin at a defined (predetermined) residual puncturing depth. Because of the elastic properties of the skin surface, the skin surface may still contact the reference element 35 after the partial retraction.

Figure 29:
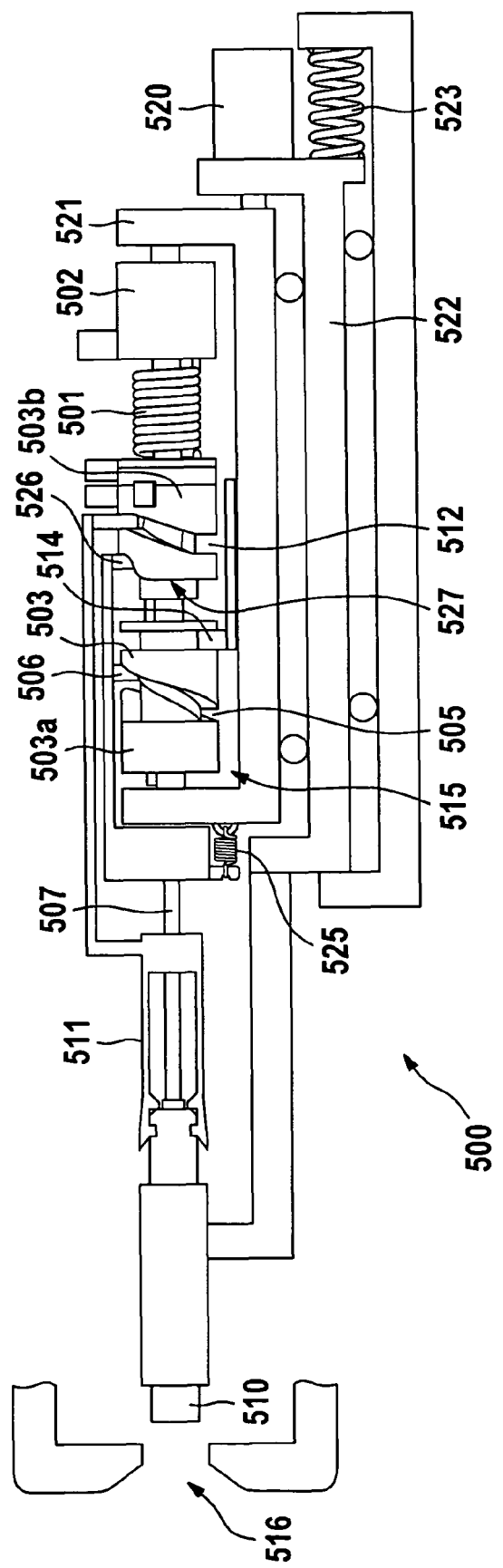
FIG. 29 shows a further exemplary embodiment of a puncturing system according to the invention in a side view.
Figure 30:
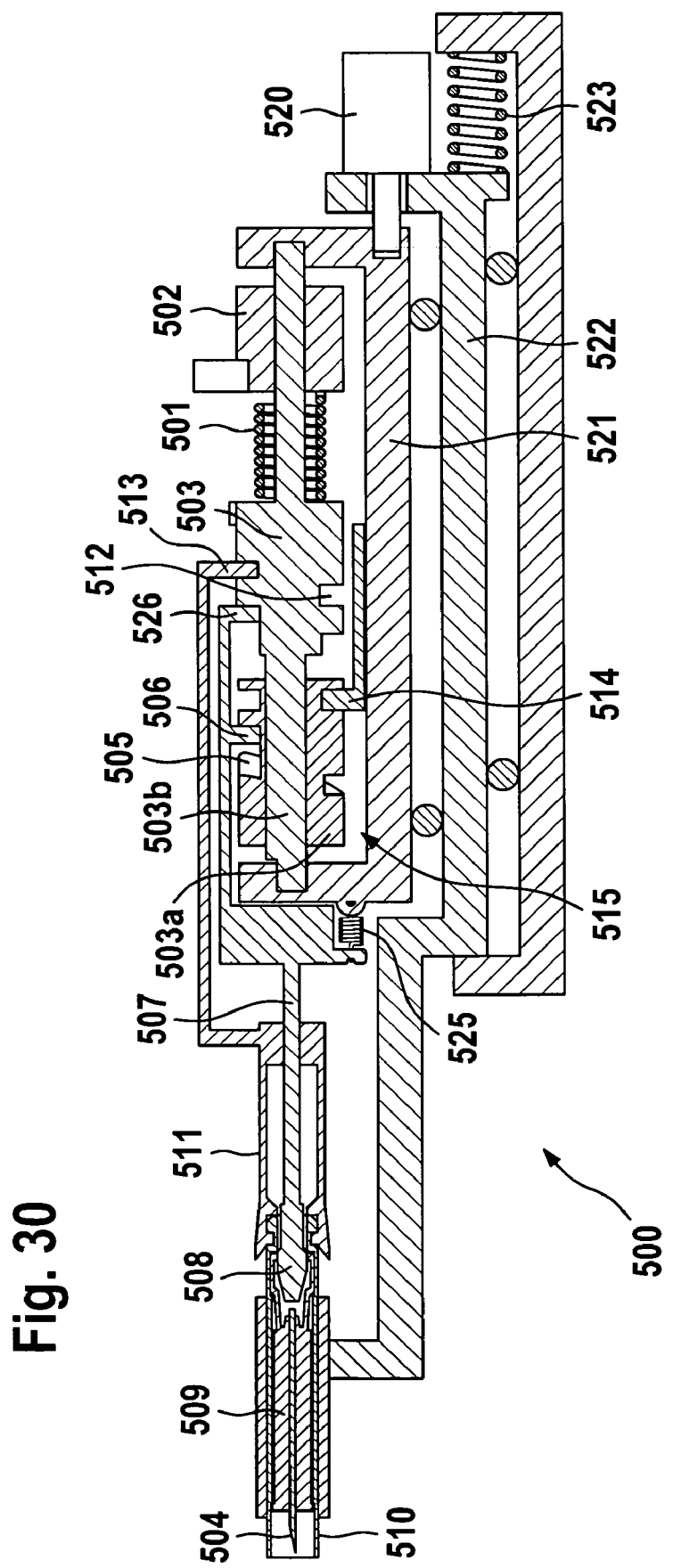
FIG. 30 shows the exemplary embodiment shown in FIG. 29 in a cross-sectional view.
Figure 31:
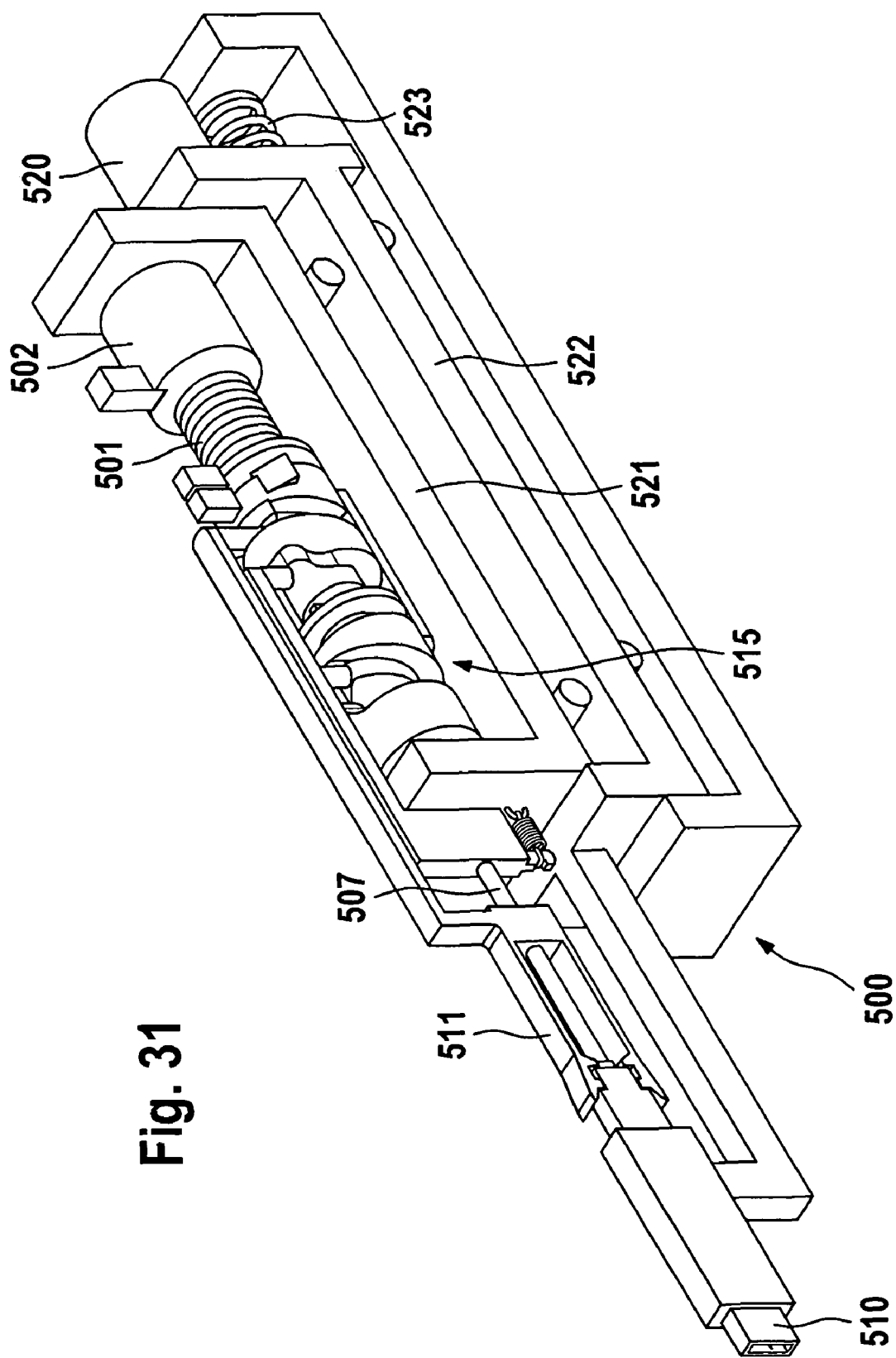
FIG. 31 shows the exemplary embodiment shown in FIG. 29 in a perspective view.

The embodiment shown in FIGS. 4 and 5 thus shows as an example that it may be advantageous if the puncturing depth reference element 35 is moved jointly (i.e., simultaneously, not necessarily equally rapidly) with the piercing element 5 only in the part of the forward phase directly preceding the reversal point. The stroke (path distance in the puncturing direction), by which the puncturing depth reference element 35 is moved jointly with the piercing element 5 until reaching the reversal point, is preferably at most 5 mm, more preferably at most 3.5 mm, and especially preferably at most 2 mm. In the design shown, this is implemented in that the puncturing depth reference element 35 rests in a rest position on a reference element bearing during the major part of the piercing movement of the piercing element 5 and is accelerated starting from this rest position in the direction toward the skin, shortly before the piercing element 5 reaches the reversal point between piercing and retraction movements. Another design, which causes similar movement behavior, is shown in FIGS. 29 through 31.

Furthermore, it is advantageous if the part of the piercing movement, during which the puncturing depth reference element 35 is moved jointly with the piercing element 5 during the forward phase (i.e., until reaching the reversal point), is passed in a very short time. This time is preferably at most 100 ms, more preferably at most 50 ms, and especially preferably at most 10 ms.

In the context of the invention it has been established that, by the above-mentioned measures, which may be used individually or in combination, on one hand the puncturing depth may be controlled precisely, and on the other hand the precise definition of the residual puncturing depth is not impaired by deformation of the skin due to the viscoelastic properties of the skin during brief contact pressure of this type. Moreover, it is advantageous if in a piercing profile of the type shown in FIG. 1, the first retraction phase R1 between reaching the reversal point (maximum puncturing depth) and the beginning of the collecting phase lasts at most 2 seconds, preferably at most 1 second, and especially preferably at most 0.5 seconds.

In the exemplary embodiment shown in FIGS. 4 and 5, the residual puncturing depth is constant during every sample collection independently of the set puncturing depth. Residual puncturing depths of 0.3 mm to 0.6 mm, preferably 0.4 mm to 0.5 mm, have been shown to be favorable. In order to achieve a defined residual puncturing depth in the puncturing instrument 20 shown, it is important that the position of the piercing element 5 in relation to the reference element 35 contacting the skin is defined by the retraction stop 38. This is achieved in the exemplary embodiment shown by locking the lancet 34 in relation to the reference element 35 by the retraction stop 38. The drive spring 21 may be used also for the retraction movement according to the exemplary embodiment shown. However, it is also possible to provide a further spring for the retraction movement. For example, a linear drive may be used for the complete retraction of the piercing element 5 out of the skin, which may also be used for tensioning the drive spring 21 before piercing and for prior detection of the Z position of the skin surface (as explained with reference to FIG. 2). Alternatively, the force to completely withdraw the piercing element 5 from the skin may also be applied to the retraction stop 38 itself or to the lancet sleeve 35.

The design shown in FIGS. 4 and 5 is an example of an embodiment of the invention in which the drive spring 21 is coupled directly only to the piercing element 5, while the reference element 35 is coupled to the piercing element 5 and thus indirectly to the drive spring 21 via a co-transport device acting in the forward phase of the piercing movement. The two stops 24 and 25 are components of the co-transport device, which contact one another in such a manner that their relative distance defines the longitudinal position of the piercing element 5 in relation to the reference element 35 and thus defines the puncturing depth, during the further forward phase until reaching the reversal point between piercing and retraction movement. The stops 24, 25 are therefore referred to as puncturing depth delimiting stops.

In the case shown, the co-transport device acts bidirectionally. It includes stops 43, 44, coupled to the piercing element 5 and the reference element 35, respectively, and acting in the retraction phase. The stops contact one another during at least a part of the retraction phase in such a manner that the position of the piercing element 5 in relation to the reference element 35 is defined thereby.

A further exemplary embodiment of a puncturing instrument 50, by which the piercing profile shown in FIG. 1 may be implemented, is shown in FIGS. 6 and 7 in a side view with an open housing 51. The puncturing instrument 50 shown is distinguished by its flat construction having an overall height of less than 4 mm. The puncturing instrument 50 includes a lancet magazine 52, in which lancets 34 are stored adjacent to one another and are pushed by a magazine spring (not shown) out of the magazine 52, for usage in sequence, into a usage position, in which they may be coupled to a pushrod 22. The lancets 34 comprise, in the typical manner, a plastic body in which a piercing element 5 is embedded, which may have one or more capillary channels for sample withdrawal. The pushrod is fastened to a carriage 54, which is movable by a spring drive 55 in a piercing and retraction movement.

The spring drive 55 includes a first leaf spring 56 as the drive spring, a second leaf spring 57 as the retraction spring, and a third leaf spring 58 as the catch spring. The leaf springs 56, 57, 58 are fastened on one end to a base plate 59, which is movable in relation to the device housing 51. The drive spring 56 carries a rotatable catch 60 on its free end, by which a movement of the drive spring 56 is transmitted to the carriage 54. For this purpose, the drive spring 56 has a cylindrical head 61 on its free end, which is seated in a matching recess of the catch 60. The catch 60 interacts with the carriage 54 via an extension face 62, which is located in the exemplary embodiment shown on a projection 63 of the carriage 54. In FIG. 6 the puncturing instrument is shown in its tensioned state before the triggering of a piercing.

The free end of the catch spring 58 presses against the catch 60 and exerts a torque on the catch 60 which is oriented clockwise in the exemplary embodiment shown. This torque ensures that the catch 60 is reliably operationally linked to the carriage 54.

The return spring 57 counteracts to the drive spring 56, i.e., it exerts a force oriented in the retraction direction on the carriage 54. The return spring 57 preferably presses against a retraction element 64 of the carriage 54, which is implemented as a projection in the exemplary embodiment shown.

The return spring 57 may be replaced by a coiled spring, which is fastened to the device housing 51 and the carriage 54. The drive 55 shown, in which the drive spring 56, the catch spring 58, and the return spring 57 are produced in one piece as a stamped part from spring steel, has the advantage of being especially cost-effective and allowing easier assembly.

To set the puncturing depth, the base plate 59 is displaced in relation to the housing 51 by a setting device (not shown). In addition to the components already described, the base plate 59 carries a pawl 65, which locks the carriage 54 in the tensioned position shown in FIG. 6.

A retraction stop 66, having an abutting element in the form of a further pawl 67, is used for stopping the piercing element 5 at the end of the retraction phase R1. Its function is explained on the basis of FIGS. 8 through 13, which show a complete working cycle of the puncturing instrument.

In order that the puncturing depth may be set independently of the residual puncturing depth, it is important that the pawl 67 of the retraction stop 66 is not fastened to the base plate 59, which is displaced in the device housing 51 for setting the puncturing depth, but rather is mounted fixed in relation to the housing, or separately settable. The pawl 67 is shown raised off of a pin 69 in FIG. 7.

FIG. 8 shows the puncturing instrument 50 having a relaxed drive spring 56. The catch 60 is first pushed back in the arrow direction F for tensioning. The sliding mechanism necessary for this purpose is not shown for the sake of better visibility. For example, a simple slider is suitable, which has an actuating element projecting out of the device housing 51 through a slot and may be pushed in the arrow direction F by a user, using a finger.

As it is pushed back, the catch 60 slides along an inclined sliding face 70 of the carriage projection 63 until the thrust face 71 formed by an undercut is reached. The catch 60 is then brought into the position shown in FIG. 7 by the catch spring 58, in which it presses against the thrust face 71 and is operationally linked to the carriage 54 in this manner. The puncturing instrument 50 is now tensioned. The force exerted by the drive spring via the catch on the carriage is absorbed by the pawl 65 in this state, so that the carriage 54 is locked in the position shown in FIG. 7 until a piercing is triggered.

A force is exerted on the pawl 65 for triggering in the direction of arrow G, so that the pawl 65, which is rotatably fastened to the base plate 59, is rotated out of its blocking position shown in FIG. 7. The triggering mechanism for actuating the pawl 65 is not shown for the sake of better visibility. For example, it may be a pin which projects out of the housing through an opening in the housing side, so that it may be pressed by a user. Alternatively, the actuating mechanism may also comprise an actuator, e.g., made of a shape-memory alloy. The precise timing control of the collecting phase is thus made easier. The pawl 65 has an elongate actuating arm 72, to which an actuating element (not shown) may be attached, so that the pawl 65 may be actuated independently of the position of the base plate 59 by pressing an actuating pin.

As soon as the pawl 65 releases the carriage 54 by a rotation, it is accelerated by the drive spring 56 in the direction of the arrow H, so that the pushrod 22, coupled to a lancet 34 and using the piercing element 5 of the lancet 34, may generate a piercing wound in a body part, typically a finger, pressed against the contact pressure face 73 of the device housing 51. The contact pressure face 73 is located as a trough-shaped depression in a lateral face of the housing 51 to make correct positioning of the affected body part easier for a user.

Upon acceleration of the carriage 54, the catch 60 oscillates on a curved path in the direction of the arrow H, driven by the drive spring 56. Because the drive spring 56 is fastened to the base plate 59 on its end facing away from the catch 60, the catch 60 increasingly moves farther away from the carriage 54 until it lifts off of the carriage 54. This is shown in FIG. 11. FIG. 11 also shows the reversal point of the lancet movement, i.e., the position at the end of the forward phase V.

During the forward phase V, the pawl 67 of the retraction stop 66 executes a rotational movement, so that the carriage 54 is stopped during the retraction movement driven by the retraction spring 57 in the position at the end of the retraction phase R1 shown in FIG. 12. This rotational movement of the pawl 67 is caused by the spring element 49 (FIG. 6), which supports the pawl 67 and the housing 51. The carriage 54 has a head 74 having a sliding face 75, against which the pawl 65 presses at the beginning of the forward phase V (FIG. 9) for this purpose. The head 74 is delimited by a step 76, against which the pawl 67 presses in the engagement position shown in FIG. 12.

The pawl 67 of the retraction stop 66 remains in the engagement position shown in FIG. 12 during the entire collecting phase S. At the end of the collecting phase S, the pawl 67 of the retraction stop 66 is actuated so that the carriage 54 is released. The carriage 54 is then retracted into its starting position by a retraction force applied by the return spring 57 during the further retraction phase R2 and the piercing element 5 is withdrawn completely from the skin.

The mechanism for actuating the pawl 67 of the retraction stop 66 is not shown for better visibility. In the simplest case, the pawl 67 may be set into rotation by a force which acts in the direction of the arrow I. A corresponding mechanism may be formed by an actuator made of a shape-memory alloy, for example. An actuator of this type may be heated by a brief current pulse above the conversion temperature of the shape-memory alloy, for example, so that a force which acts in the direction of the arrow may be generated by a shape change caused thereby.

Figure 14:
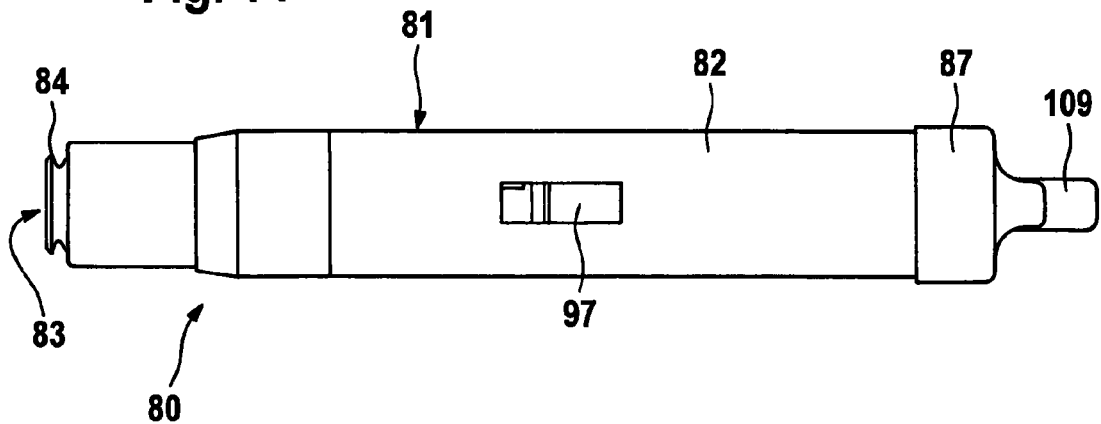
FIG. 14 shows a further example of a puncturing instrument according to the invention in a side view.
Figure 15:
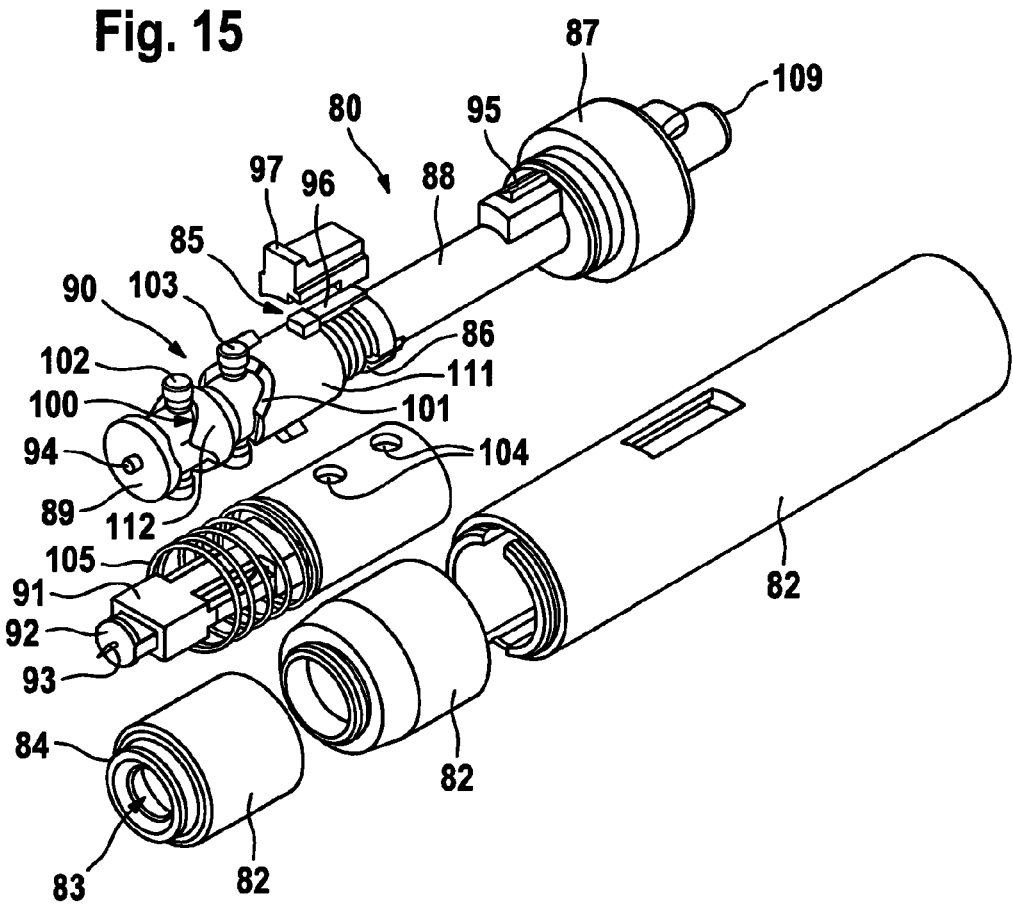
FIG. 15 shows the example shown in FIG. 14 in an exploded view.

A further exemplary embodiment of a puncturing system 80 is shown in FIG. 14 in a side view and in FIG. 15 in an exploded view. The puncturing instrument 81 belonging to the puncturing system has a housing 82 having a housing opening 83, which is enclosed by a contact pressure ring 84, which elastically deforms when pressed against a body part. For example, the contact pressure ring 84 may be produced from a rubber-elastic plastic. The contact pressure ring 84 preferably has an inwardly inclined contact pressure face, adapted for applying a finger or another body part thereto. A suitable contact pressure ring 84 is described in detail as a compression unit in WO 01/89383A2, which is incorporated herein by reference.

The puncturing instrument 81 comprises a spring drive 85 having a drive spring 86, which is tensioned by rotating a tensioning knob 87 projecting out of the housing. The tensioning knob 87 forms the head of a tensioning rotor 88, which is coupled to the drive spring 86. The drive spring 86 is coupled to a drive rotor 89, whose rotational movement is converted by means of a control device 90 into a piercing and retraction movement of a lancet holder 91. The lancet holder 91 holds a replaceable sample collection unit 92, which is implemented as a lancet having a piercing element 93 embedded in a plastic body.

After usage, a sample collection unit 91 may be detached from the lancet holder by means of an ejection rod 94 and pushed out of the housing opening 83. The ejection rod 94 is guided through a central opening of the drive assembly formed by the tensioning rotor 88 and the drive rotor 89, so that a used sample collection unit 92 may be ejected by pressing an ejection knob, which is formed by the head 109 of the ejection rod 94 projecting out of the housing 82.

The tensioning rotor 89 carries a pawl 95, which cooperates with a ratchet implemented on the inner wall of the housing 82 in such a manner that the tensioning rotor 88 may only rotate in one direction. During tensioning of the drive spring 86, a movement of the drive rotor 89 is prevented by a blocking device 96. By actuating the triggering element 97 projecting out of the housing 82, and implemented as a slider in the example shown, the blocking device 85 is released, so that the drive rotor 89 rotates and a piercing and retraction movement is triggered.

In this embodiment it may again be advantageous to adapt the piercing movement to different positions of the skin surface (within the range of the "Z-variance") by means of a prior detection of the skin surface. This may be performed, for example, in that only the contact pressure ring 84 is fixed to the housing 82, while the mechanism shown may be moved in the housing 82 in the longitudinal direction by means of a linear drive. This linear drive is used for the purpose of setting the mechanism in such a manner that the desired residual puncturing depth is ensured after the piercing (cf. also FIGS. 29 through 31).

In the exemplary embodiment shown the piercing profile shown in FIG. 1 is achieved by means of the control device 90 explained hereafter on the basis of FIGS. 16 through 21. The control device 90 comprises a curve controller, by which a rotational movement of the drive rotor 89 is converted into a piercing and retraction movement of the lancet holder 91.

In the exemplary embodiment shown, the drive rotor 89 carries a first control curve 100 and a second control curve 101. First and second control curve travelers 102, 103 travel along the control curves 100, 101 and are moved in the puncturing direction by the rotational movement of the drive rotor 89. In principle, one first and one second control curve traveler 102, 103 would be sufficient. However, two first control curve travelers 102 and two second control curve travelers 103 are provided to avoid tilting torques. In the exemplary embodiment shown the control curve travelers 102, 103 are implemented as pins, which are inserted into matching recesses 104 of the lancet holder 91. The control curve travelers 102, 103 may, however, also be implemented in one piece with the lancet holder 91.

Figure 16:
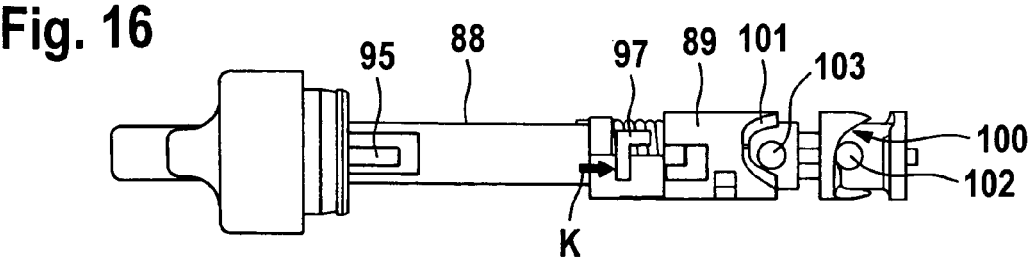
FIG. 16 shows the control device of the example shown in FIG. 14 at the beginning of the forward phase.

The position of the control curve travelers 102, 104 in relation to the drive rotor 89 at the beginning of the forward phase is shown in FIG. 16. The lancet holder 92 with its control curve travelers 102, 103 is biased towards the drive rotor 89 by means of the compression spring 105, which is supported on the housing 84. At the beginning of the forward phase, the first control curve traveler 102 presses against the first control curve 100. In the starting position shown in FIG. 1, the second control curve traveler 103 does not press against the second control curve 101 because of the distance between the first control curve 100 and the second control curve 101. To trigger a piercing movement, the actuating element is displaced in the direction of the arrow K, so that the blocking device 96 is released and the drive rotor 89 begins to rotate.

Figure 17:
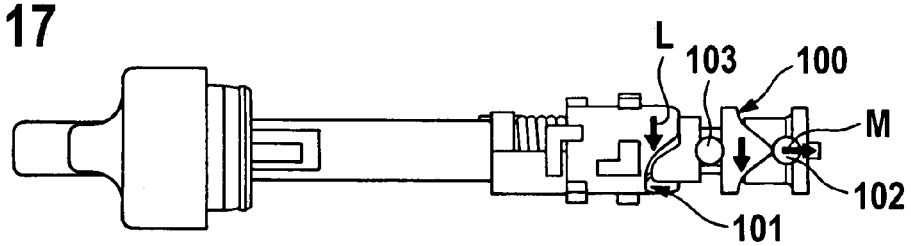
FIG. 17 shows the control device shown in FIG. 16 at the end of the forward phase.

During the forward phase V, the drive rotor 89 rotates in the direction of the arrows L shown in FIG. 17. This causes the first control curve traveler 102 to be moved by the rising flank of the first control curve 100 in the puncturing direction, which is shown by the arrow M. The distance between the second control curve traveler 103 and the second control curve 101 increases during this movement because the control curve travelers 102 and 103 are fixed to the lancet holder 91. The position of the control curve travelers 102, 103 at the end of the forward phase V is shown in FIG. 17. In this position, the lancet holder 91 has reached the maximum stroke, so that a piercing element 93 fastened thereto projects at the set puncturing depth into the skin of a patient.

Figure 18:
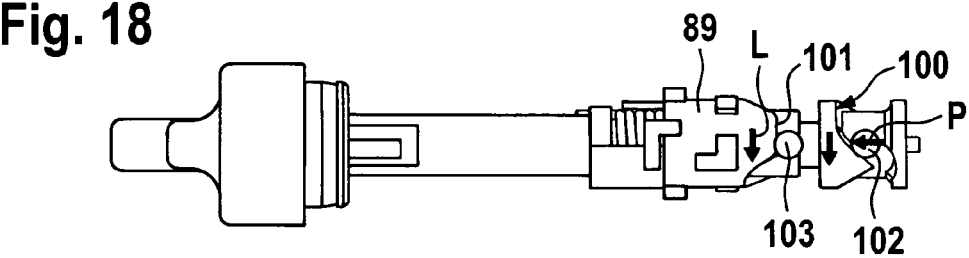
FIG. 18 shows the control device shown in FIG. 16 at the end of the retraction phase.

During the retraction phase R1 shown in FIG. 18, the falling flank of the first control curve 100 causes the first control curve 102 and thus also the lancet holder 91 connected thereto to execute a retraction movement in the direction of the arrow P. This retraction movement is stopped when the second control curve traveler 103, as shown in FIG. 18, comes into contact with the second control curve 101.

Figure 19:
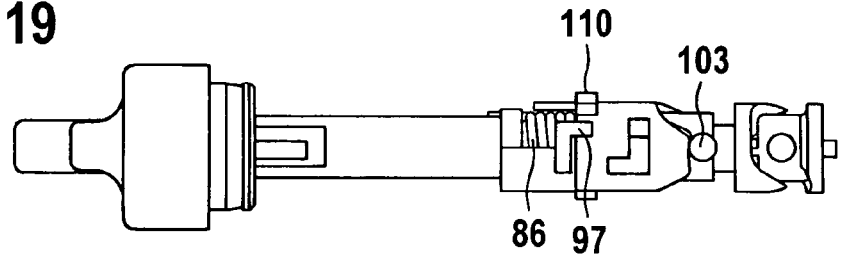
FIG. 19 shows the control device shown in FIG. 16 during the collecting phase.
Figure 20:
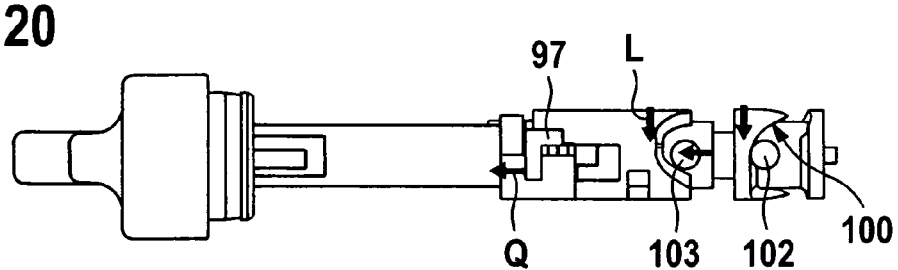
FIG. 20 shows the control device shown in FIG. 16 during the further retraction phase.
Figure 21:
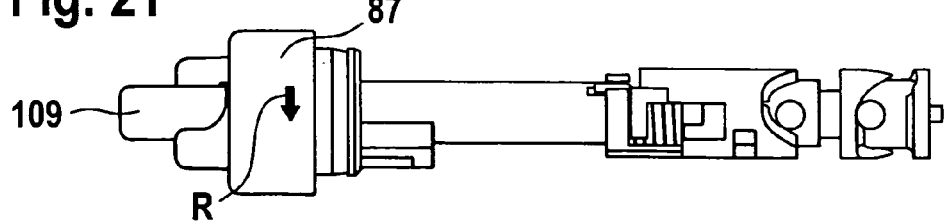
FIG. 21 shows an illustration corresponding to FIG. 16 during tensioning of the drive spring.

During the further rotation of the drive rotor 89 in the direction of the arrow L, the movement of the lancet holder 91 is defined by the second control curve 101, because, in the relevant rotational angle range, it has an essentially flat course, while the first control curve 100 drops further. As shown in FIG. 19, the first control curve traveler 102 thus looses contact with the falling flank of the first control curve 100. In this state, the rotational movement of the drive rotor 89 is stopped by a retraction stop 110, which, in the exemplary embodiment shown, is implemented as a projection located on the drive rotor 89, which impacts against a trigger slider 97. In this manner, the movement of the lancet holder 91 is stopped for the collecting phase.

After a short time, the collecting phase is ended by releasing the retraction stop 110. For this purpose, the trigger slider 97 is pushed back in the direction of arrow Q, so that the drive rotor 89 is again set into motion in the direction of arrow L by the residual tension of the drive spring 86. In this second retraction phase, the second control curve traveler 103 contacts a falling flank of the second control curve 101 until the first control curve traveler 102 contacts the first control curve 100. In this manner, the lancet holder 91 and thus also the first and second control curve travelers 102, 103 again reach the starting position shown in FIG. 16. The drive spring 86 may subsequently be tensioned again by rotating the drive knob 87 in the direction of arrow R.

Figure 22:
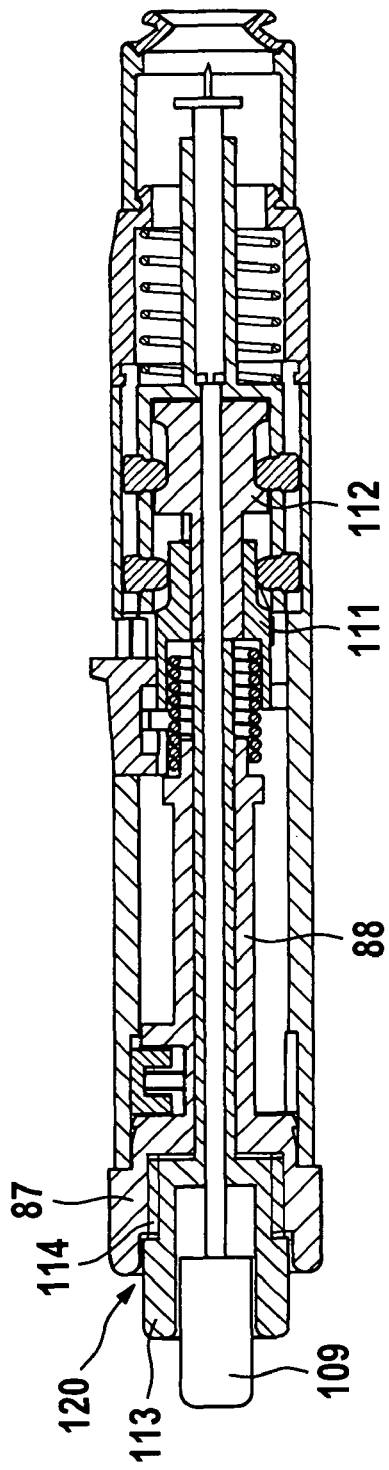
FIG. 22 shows a cross-section of the exemplary embodiment shown in FIG. 14 at maximal setting of the puncturing depth.
Figure 23:
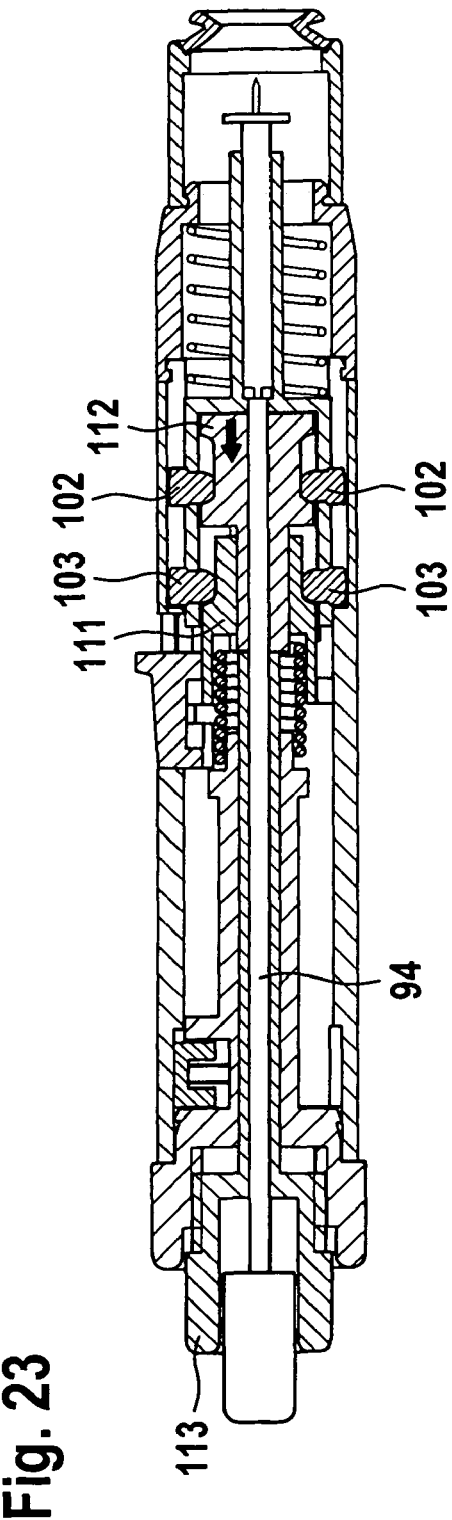
FIG. 23 shows a corresponding cross-sectional illustration at minimal setting of the puncturing depth.

In the described control device, the puncturing depth is a function of the distance between the first control curve 100 and the second control curve 101. Therefore the second control curve 101 is located on a first part 111 of the drive rotor 89, which may be displaced in relation to a second part 112 of the drive rotor 89. The second part 112 carries the second control curve 101. A setting device 120 having a set screw 113 is provided for shifting the two parts 111, 112 of the drive rotor 89 in relation to one another. By rotating the set screw 113 in the thread 114, the position of the first part 111 of the drive rotor 89 may be adjusted in the puncturing direction in relation to the second part 112 of the drive rotor 89. For illustration a longitudinal section of the puncturing instrument 81 at maximal setting of the puncturing depth is shown in FIG. 22 and a sectional view of the puncturing instrument 81 at minimal setting of the puncturing depth is shown in FIG. 23.

To make the tensioning of the drive spring 86 easier for a user, the described device 81 may be equipped with an electric motor. In this case, the tensioning knob 87 of the tensioning rotor 88 may be omitted, because the tensioning rotor 88 is rotated by means of the electric motor to tension the drive spring 86. The collecting phase may be ended automatically by releasing the retraction stop 110 at the end of the collecting phase, by means of a timing circuit and a magnetic coil or another electromechanical actuating element.

In the exemplary embodiment shown, a 180° drive is used, in which the entire sequence is controlled by a half rotation of the rotors. The control pins 102 and 103 are accordingly each provided twice. Alternatively, the sequence may also be controlled by a complete rotation, in which case only one control pin 102 and 103 each is used. The control using a complete rotation of 360° has the advantage that the axial movement stroke is distributed on a relatively large peripheral distance and therefore the angle of inclination is flatter. Of course, it is also possible to work with three control pins 102 and 103 each and a control by means of a 120° rotation, having appropriately adapted control curves.

Figure 24:
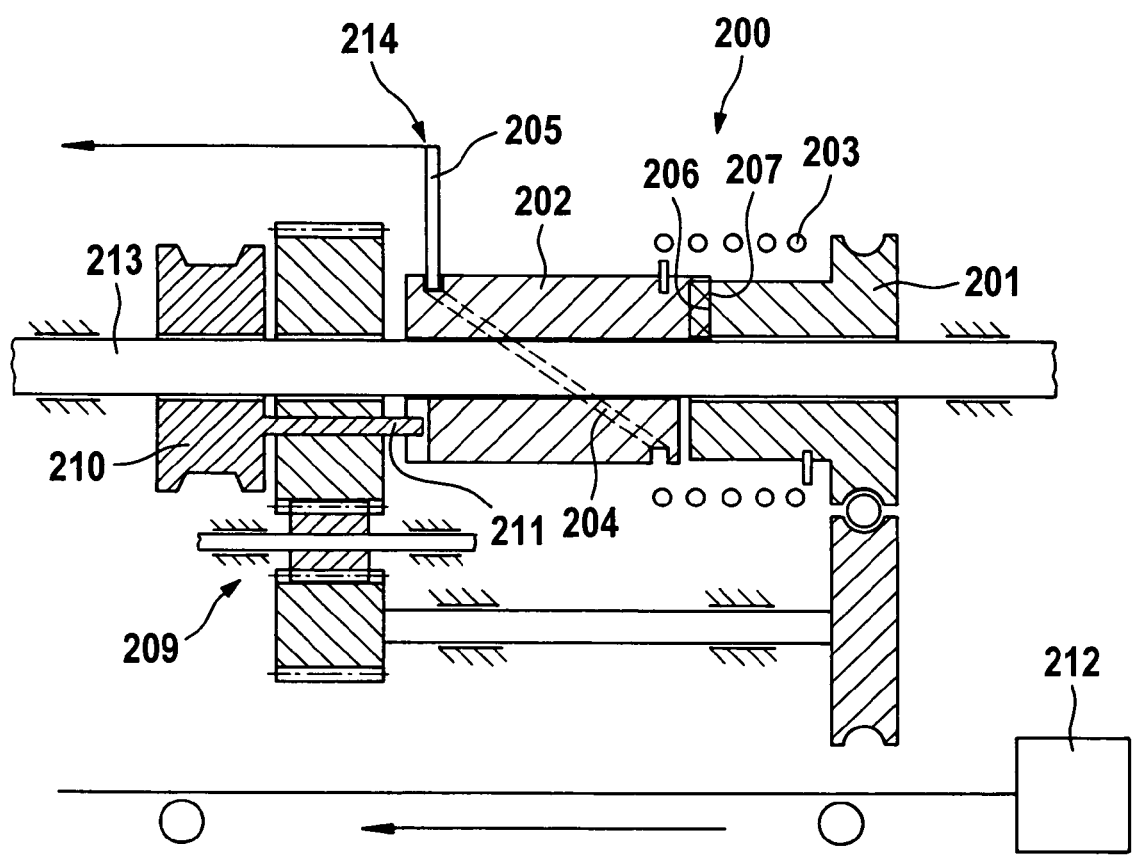
FIG. 24 shows a further exemplary embodiment in a cross-sectional illustration.

A further exemplary embodiment of a spring drive 200 and a control device, by which the piercing profile shown in FIG. 1 may be implemented, is shown in FIG. 24 in a cross-sectional view. The remaining parts of the puncturing instrument, in particular the housing, operating elements, and lancet holder, are not shown for simplification.

Similarly as in the exemplary embodiment described on the basis of FIGS. 14 through 23, the spring drive 200 of the exemplary embodiment shown in FIG. 24 comprises a tensioning rotor 201 and a drive rotor 202, which is coupled to the tensioning rotor 201 via a drive spring 203. The drive rotor 202 carries a control curve 204 in the form of a groove along which a control curve traveler 205 travels during a piercing and retraction movement. The control curve traveler 205 is connected to a lancet holder (not shown), so that a rotational movement of the drive rotor 202 may be converted into a piercing and retraction movement of the piercing element.

The drive rotor 202 and the tensioning rotor 201 have stop parts 206, 207, which abut against one another in the starting position shown in FIG. 24. The stop parts 206, 207 serve for bearing a pre-tension of the drive spring 208 and stopping a rotational movement of the drive rotor 202 at the end of the retraction phase R1.

In the starting position shown in FIG. 24, the control curve traveler 205 is located in an extreme position, which corresponds to a maximal stroke of a lancet holder (not shown). To set the puncturing depth, the drive rotor 202 is rotated, by means of setting device 209, out of the starting position in relation to the tensioning rotor 201 by a rotational angle α so that the control curve traveler 205 travels along the control curve 204 and a piercing element (not shown) fastened to the lancet holder is retracted by a distance corresponding to the rotational angle α. This may be accomplished, for example, by worm 215 driven by a motor comprised in the setting device 209.

The rotational angle α is selected in such a manner that the control curve traveler 205 is retracted by the desired puncturing depth dm plus a constant starting distance. If the control curve 204 (as in the exemplary embodiment shown) has a constant slope, the rotational angle α is the sum of a rotational angle α1, which causes a lancet stroke in the amount of the desired puncturing depth, and a rotational angle α2, which causes a lancet stroke corresponding to the starting distance of the lancet. As soon as the control curve traveler 205 has reached the desired position, the position of the drive rotor 202 is locked. A starting stop 211, via which the drive rotor 202 was rotated into the desired position, may be used for this purpose.

Simultaneously with or after the rotation of the drive rotor 202, the tensioning rotor 201 is rotated in the opposite direction. The drive rotor is pivoted by a rotational angle α−α2−β=α1−β in relation to the starting position shown in FIG. 22, the rotational angle β corresponding to a lancet stroke in the amount of the desired residual puncturing depth. The tensioning rotor 201 is then locked in the resulting rotational angle position.

The last step for setting the puncturing depth is that the entire drive 200 is shifted by means of an electric motor 212 along the guide 213 in the puncturing direction until the distance between the tip of the piercing element and the skin surface corresponds to the starting distance. As soon as this position is reached, a piercing may be initiated by releasing the lock 211 of the drive rotor 202. The drive rotor 202 then rotates until its rotational movement is stopped by impact of the stop parts 206, 207 of the drive rotor 202 and the tensioning rotor 201 against one another.

During the forward phase V, the drive rotor 202 rotates around the rotational angle α back into the position shown in FIG. 24. This causes, via the control curve traveler 205, a stroke of the piercing element in the amount of the desired puncturing depth plus the starting distance, the latter corresponding to the distance between the skin surface and the piercing element upon triggering of the piercing movement. During the subsequent retraction phase R1, the drive rotor 202 passes through a rotational angle range α−α2−β=α1−β, so that the resulting retraction movement of the piercing element causes that the piercing element remains stuck in the skin at the predefined residual puncturing depth, as soon as the drive rotor 202 is stopped by the stop parts 206, 207. Thereby the collecting phase is initiated.

By setting the positions of the drive rotor 202 and the tensioning rotor 201 before the triggering of a piercing, an active section of the control curve 204 is selected, along which the control curve traveler 205 travels during the forward phase V and the retraction phase R1. The start of the active section defines the puncturing depth, and the end of the active section defines the residual puncturing depth. An inactive section lies before the active section. With increasing puncturing depth setting this inactive situation becomes smaller. A second inactive section lies after the active section, which is smaller with a smaller setting of the residual puncturing depth. Thus, the control curve traveler 205, the control curve 204, the stop parts 206, 205, and the starting stop 211 form a control device 214 for controlling the piercing and retraction movement.

The distance between the tip of the piercing element and the skin surface may be determined by a resistance measurement and/or capacitive and/or inductive measurement, in which the tip of the piercing element is preferably used as an electrode.

A further possibility for setting the puncturing depth comprises to rotate the drive rotor 202 always by the same angle α out of the starting position shown in FIG. 24, i.e., always locking it in the same position. This position is preferably selected in such a manner that the control curve traveler 205 is retracted as far as possible. In this case, the position of the skin surface is first determined in relation to a fixed reference point of the device housing and the drive 200 is thereafter moved so far in the puncturing direction that the lancet stroke occurring during the forward phase results in the desired puncturing depth. The tensioning rotor 201 must be set by means of its stop part in such a manner that the residual puncturing depth is ensured. Both electronic means (position sensors) and also mechanical means (a link controller coupled to the puncturing depth setting) may be used for this purpose.

After the end of the collecting phase, the piercing element is withdrawn completely from the skin by rotating the tensioning rotor 201 in the appropriate direction. Due to the pre-tension of the drive spring 203, the drive rotor 202 follows the rotational movement of the tensioning rotor 201, so that the control curve traveler 205 travels along the remaining section of the control curve 204 and thereby causes a retraction movement of the piercing element. A linear drive may alternatively be used for the prior detection of the position of the skin surface and for the retraction phase R2.

Figure 25:
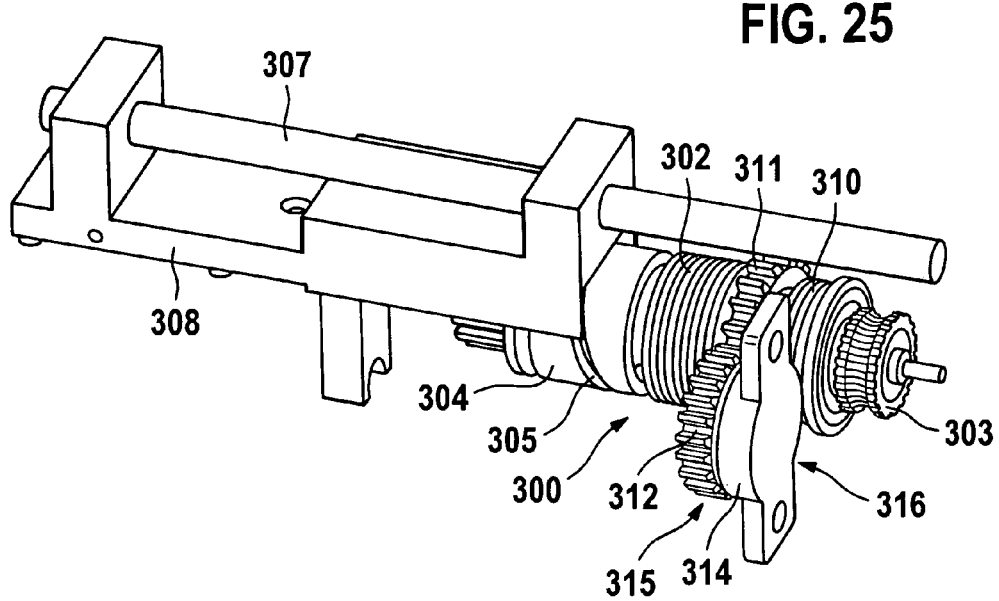
FIG. 25 shows a further exemplary embodiment in a perspective view.

Abrupt stopping of the piercing element at the end of the retraction phase may cause painful vibrations in certain circumstances. Therefore preferably a damper is used for decelerating the retraction movement. An exemplary embodiment of a drive 300 which is coupled to a damping mechanism 315 is shown in FIG. 25 in a perspective view, in FIG. 26 in a cross-sectional view, and in FIG. 27 in a side view. The damping mechanism 315 comprises a damping rotor 301, which is coupled via sprockets 311, 312 to a rotation damper 316. The rotation damper is formed by a rotating body 313 and a housing 314 filled with damping liquid.

Like the drive 200 described on the basis of FIG. 24, the drive 300 shown here comprises a drive spring 302, a tensioning rotor 303 for tensioning the drive spring 302, and a drive rotor 304 driven by the drive spring 302. The drive rotor 304 carries a control curve 305 along which a control curve traveler 306 of a curve controller travels during a piercing movement and which causes a piercing and retraction movement of a lancet holder 307, which is guided by a guide 308 to be movable in the puncturing direction.

The drive 300 additionally comprises a damping rotor 301, which is located between the drive rotor 304 and the tensioning rotor 303. The tensioning rotor 303, the damping rotor 301, and the drive rotor 305 have, like the rotors 201, 202 of the exemplary embodiment explained on the basis of FIG. 24, stop parts, by which adjacent rotors press against one another and which bear the pre-tension of the drive spring 302. These stop parts are not shown in FIGS. 23 through 25, but correspond in their design to the stop parts 206 and 207 shown in FIG. 24.

The drive 300 additionally comprises a damping spring 310, which acts between the tensioning rotor 303 and the damping rotor 301. The pre-tension of the damping spring 310 is less than the pre-tension of the drive spring 302 and counteracts the force of the drive spring 302. The spring force of the damping spring 310 thus acts so that the stop parts of the intermediate rotor 301 and the tensioning rotor 303 move away from one another by a relative rotational movement of the two rotors 301, 303, but this is prevented by the stronger spring force of the drive spring 302.

The damping rotor 301 carries a sprocket 311 on its exterior side, which is coupled via a sprocket 312 to a damper shaft 313, which may rotate in the housing 314, which is filled with a viscous liquid and thus forms a damping bearing.

Figure 26:
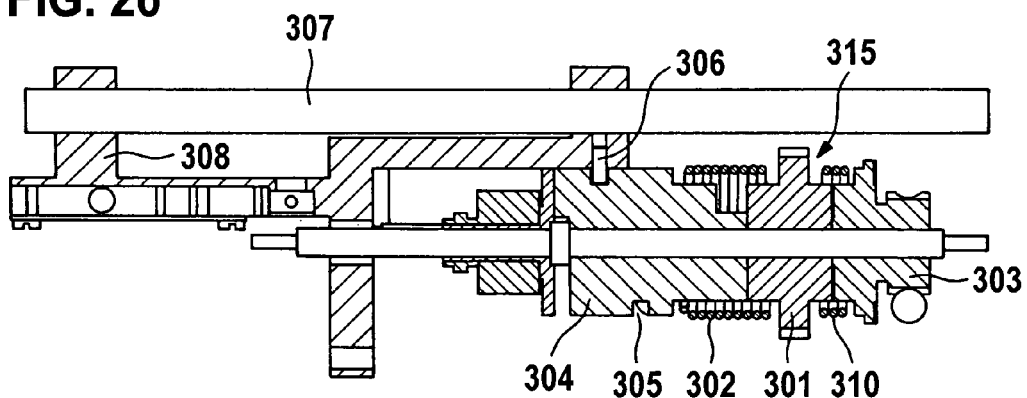
FIG. 26 shows the exemplary embodiment shown in FIG. 25 in a cross-sectional view.
Figure 27:
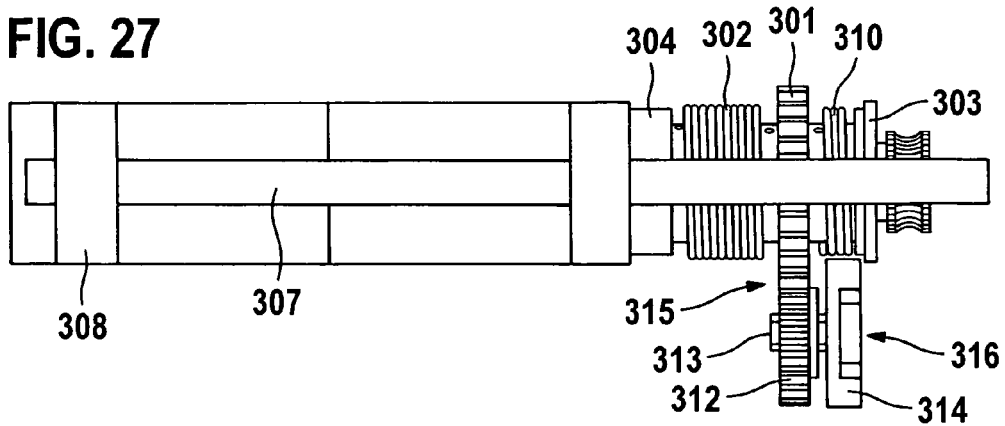
FIG. 27 shows the exemplary embodiment shown in FIG. 25 in a side view.

In the exemplary embodiment shown in FIGS. 25 to 27 the puncturing depth and the residual puncturing depth may be set in the same manner as in the exemplary embodiment described on the basis of FIG. 24. The only difference is that the drive rotor 305 is not stopped directly by a stop part of the tensioning rotor 303 at the end of the retraction phase R1, but rather its stop part impacts against a stop part of the damping rotor 301. To avoid repetitions, the movement sequence of the individual rotors is not explained hereafter with respect to the residual puncturing depth, but rather only with respect to the special features caused by the damping rotor 301.

During tensioning of the drive spring 302, the tensioning rotor 303 is rotated in relation to the intermediate rotor 301. This has the result that the stop parts of the tensioning rotor 303 and the damping rotor 301 and of the drive rotor 304 and the damping rotor 301 lift off of one another. At the end of the tensioning procedure, the damping rotor 301 is rotated by an angle χ in relation to the tensioning rotor 303 because of the damping spring 310.

If a piercing is triggered, the drive rotor 304 rotates so that a lancet holder 307 executes a piercing and retraction movement corresponding to the preceding exemplary embodiment due to the curve controller 305, 306. At the end of the retraction phase, the stop parts of the drive rotor 304 and the damping rotor 301 impact one another, so that the damping rotor 301 is also set into rotation. This rotational movement is counteracted by the tension of the damping spring 310. The damping rotor 301 is additionally braked via the sprocket 312 and the shaft 313 mounted in the damping bearing 314.

At the end of the retraction phase R1, the stop parts of the damping rotor 301 and of the tensioning rotor 303 again abut against one another, so that the rotational movement of the drive rotor 304 and thus also the retraction movement of the lancet holder 307 are stopped. To define the residual puncturing depth precisely, the tensioning rotor 303 is locked, for example by catching against the device housing (not shown) by means of a pawl or by engaging with a self-locking gear.

Instead of a gearwheel coupling 311, 312 of the damping rotor 301 with the shaft 313 guided in the damping bearing 314, a damper may also be integrated in the damping rotor 301 and the tensioning rotor 303 to stop the rotational movement of the drive rotor 304 in a damped manner at the end of the retraction phase R1. The damping bearing 314, or also a damper integrated in the damping rotor 301, may be implemented using a commercially available rotation damper, for example. A damping effect is typically achieved by means of a rotating body which rotates in viscous oil, such as silicon oil, which is enclosed by a housing wall. The strength of the damping effect is a function of the oil viscosity and the distance of the rotating body, such as the shaft 313, from the housing wall of the damper, such as the bearing 314. If the rotating body is implemented as a stack of flat disks which each have a fixed distance to one another, and if a corresponding configuration of plates is inserted into the housing, which may rotate in the intermediate spaces between the rotating disks, the damper characteristic may be altered by more or less interleaving of the plates and the disks. Damping as a function of rotational angle may also be advantageous. It may be implemented, for example, in that the radius or the thickness of the interleaving plates and disks varies around their circumference.

Figure 28:
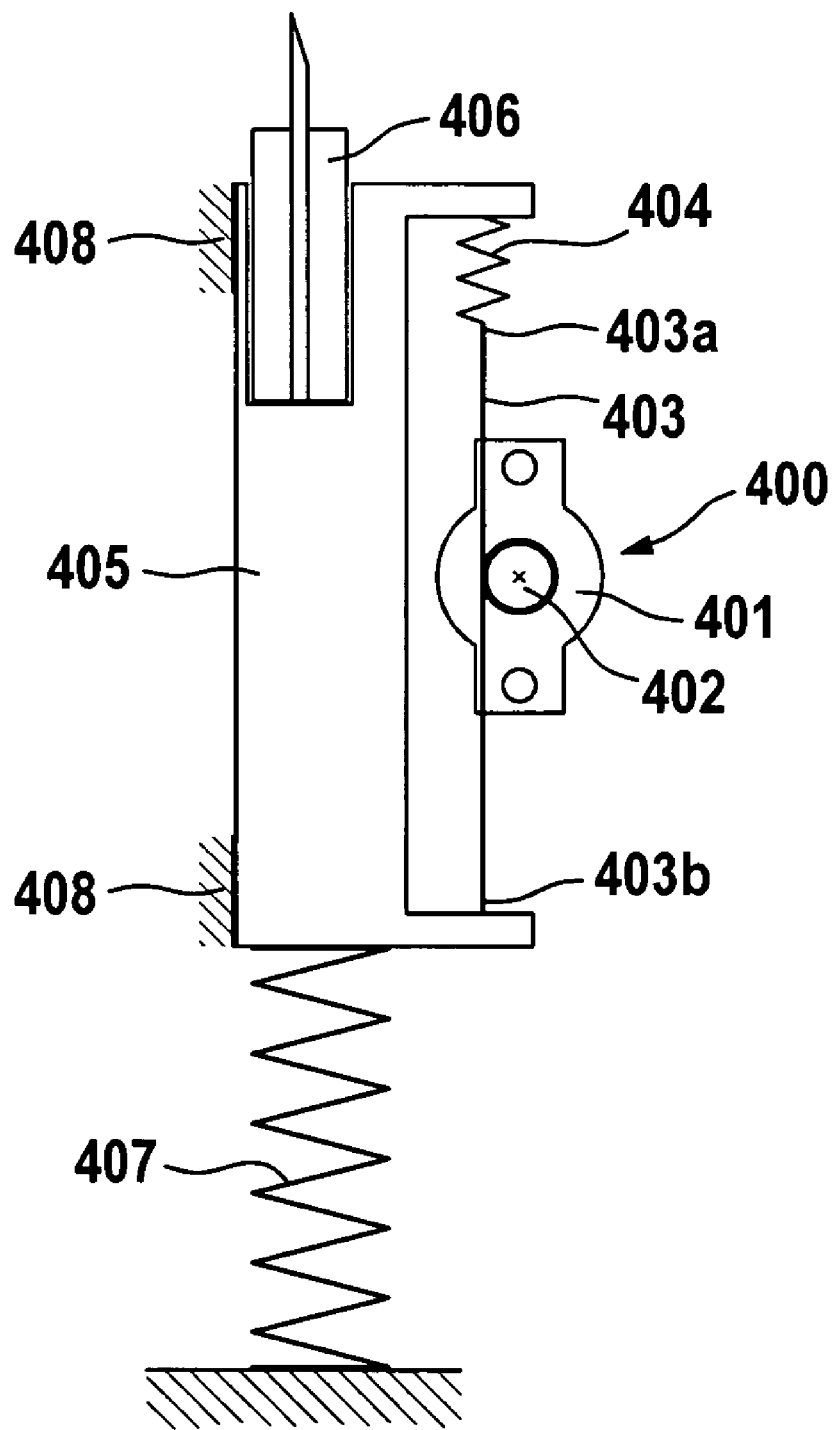
FIG. 28 shows a further exemplary embodiment of a drive having a damping mechanism.

A further exemplary embodiment of a damping mechanism is shown in FIG. 28. It may be used in the exemplary embodiment explained on the basis of FIGS. 4 and 5, for example, to prevent abrupt stopping at the end of the retraction movement by damping. The damping mechanism 400 comprises a rotation damper 401 having a rotating body 402 in the form of a shaft, which is coupled via a filament 403 and a spring 404 to a lancet holder 405. The filament 403 is wound around the shaft 402 and is fixed to the lancet holder 404 at one end 403a, while its other end 403b is coupled to the lancet holder 405 via the spring 404. If the lancet holder 405 is at rest, before the triggering of a piercing movement, for example, the filament 403 is tensioned tautly by the spring 404.

During a piercing movement, the lancet holder 405 and thus also the sample collection unit 406 inserted therein are accelerated by means of a drive spring 407 in the puncturing direction on a piercing path predefined by linear guides 408. This has the result that the rear end 403b of the filament 403 is relieved, while the spring 404 is tensioned further by the piercing movement of the lancet holder 405. Consequently the spring force exerted by the spring 404 on the filament 403 increases, so that the filament 403 is moved in relation to the shaft 402. Because no force is exerted on the rear end of the filament 403b by the lancet holder 405, the filament may slide on a shaft 402 with a low friction force, so that the forward movement of the lancet holder 405 is only slightly braked by the rotating damper 401.

In a subsequent retraction phase, during which the drive spring 407 exerts with suitable dimensioning a traction force on the lancet holder 405, a traction force is exerted on the rear end 403b of the filament 403 by the lancet holder 405. The front end 403a of the filament 403 is tensioned tautly by the spring 404. This causes the loops of the filament 403 to press tautly against the shaft 402. A significantly higher friction force thus exists between the filament 403 and the shaft 402 during the retraction phase than during the forward phase. Therefore, the filament 403 may not slide or may only slide slightly on the shaft 402 during the retraction phase. The traction force exerted by the lancet holder 405 on the rear end 403b of the filament 403 is therefore transmitted by friction forces to the shaft 402 and causes a torque by which the shaft 402 is set into rotation. The shaft 402 forms the rotating body of the rotation damper 400 and is mounted to be rotatable in the chamber 401 in a damping liquid, for example, a viscous oil. In this manner, the kinetic energy of the lancet holder 405 may be absorbed and dissipated by the rotation damper 400 during the retraction movement, so that a damped retraction movement, with slow stopping, results.

Instead of coupling the damping mechanism to the lancet holder 405, it may also be coupled to the reference element 35 which in the exemplary embodiment described in FIGS. 4 and 5, for example is implemented as a sleeve. Specifically, if the reference element is also retracted during the retraction phase by the lancet holder, the movement of the lancet holder may also be braked by damping applied to the reference element. If the reference element is already pressed against the skin surface by the user during a piercing, a freewheeling function of the damping mechanism, which is achieved in the exemplary embodiment described on the basis of FIG. 28 in that the filament 403 loops around the shaft 402, is not provided. In a case of this type, it is sufficient to couple the reference element by means of a toothed rack to the shaft 402 of the rotation damper forming the rotating body, for example, or directly to a corresponding linear damper.

A further exemplary embodiment of a puncturing system 500, by which the piercing profile shown in FIG. 1 may be implemented, is shown in FIG. 29 in a side view, in FIG. 30 in a cross-sectional view, and in FIG. 31 in a perspective view. The drive 515 of the puncturing instrument shown includes a drive spring 501, a tensioning rotor 502 for tensioning the drive spring, and a drive rotor 503 driven by the drive spring 501. A control device in the form of a curve controller is used for converting a rotational movement of the drive rotor 503 into a piercing and retraction movement of a piercing element 504. A lancet control curve 505 is implemented as a groove in the drive rotor 503. A lancet control curve traveler 506 in the form of a pin engages in the control curve 505, travels along it and is connected to a lancet holder 507. The lancet holder 507 has a head 508, which catches in a formfitting manner with a sample collection unit 509, to which the piercing element 504 belongs.

As in the exemplary embodiment described on the basis of FIGS. 4 and 5, the sample collection unit 509 is inserted into the puncturing instrument together with a reference element 510 in the form of a sleeve. During piercing, the reference element 510 contacts the skin of a user and thus ensures a reference point for defining the puncturing depth.

The reference element 510 is connected by interlocking with a reference element carrier 511, whose movement is controlled by a curve controller having a reference control curve 512 and a reference control curve traveler 513. The control curve 512 is again embodied as a groove in the drive rotor 503, and the control curve traveler 513 of the reference element carrier 511 engages therein. To set the puncturing depth, the distance of the two control curves 505, 512 can be adjusted by means of a setting device 514 in the form of an adjustable axial mount. Similarly as in the exemplary embodiment explained on the basis of FIG. 14, the two control curves 505, 512 are located on a first part 503a of the drive rotor 503 and on a second part 503b of the drive rotor 503, respectively. Using the setting device 514, the distance between the first part 503a of the drive rotor 503 and the second part 503b of the drive rotor 503 may be varied.

For piercing, a housing opening 516, only schematically indicated in FIG. 29, of the puncturing instrument is pressed against a skin surface of the user and the distance of the reference element 510 from the skin surface is adjusted. For this purpose, a first carriage 521 can be shifted in the puncturing direction, on which the drive 515 and thus also the lancet holder 507 and the reference element carrier 511 are mounted. It is moved toward the skin surface by means of an electric motor 520 until the reference element 510 contacts the skin. This may be detected electronically, for example, by an inductive or capacitive measurement. The carriage is subsequently retracted somewhat, until the distance to the skin surface has a predefined value.

After the triggering of a piercing, the lancet holder 507 and the reference element carrier 511 are moved forward during the forward phase by a rising flank of the corresponding control curve 505, 512. During the actual piercing procedure, i.e., during the penetration of the piercing element 504 into the skin surface, the reference element 510 contacts the skin surface so that a reference point for a precise puncturing depth is defined. Because the elastic properties of the skin surface are different from patient to patient and are also a function of the piercing point itself, the first carriage 521 is mounted on a second carriage 522, which may be pushed back against a contact pressure control spring 523. A maximum contact pressure is defined by the contact pressure control spring 523, which may act via the reference element 510 on the skin surface. Higher contact pressures are compensated for by a displacement of the second carriage 522 against the contact pressure control spring 523.

After reaching the maximum puncturing depth, the lancet holder 507 and the reference element carrier 511 are retracted. The curve controller of the lancet holder 507 has the special feature that the lancet control curve traveler 506 disengages during the retraction movement from its engagement with the control curve 505. This means that the control curve traveler is not, as otherwise typical, guided along the entire control curve in such a manner that every position of the control curve traveler on the control curve corresponds to a defined longitudinal position of the traveler and thus of the controlled element (piercing element, reference element) in the puncturing direction. Rather, the longitudinal position of the control curve traveler and thus the controlled element upon released engagement of the control curve is, after the disengagement with the control curve occurred, at most delimited in one spatial direction (opposite to the puncturing direction or in the puncturing direction), but is free at least in the opposite spatial direction. In the exemplary embodiment shown this is achieved in that the groove forming the control curve is widened on the returning flank to such an extent that the control curve traveler 506 is no longer guided there. The lancet holder 507 is therefore not actively retracted by the lancet control curve traveler 506 during the retraction phase.

Instead, the lancet holder 506 is retracted by a restoring spring 525. The restoring spring 525 couples the lancet holder 507 to the first carriage 521 and thus also to the drive. During the retraction phase, the lancet holder 507 is therefore moved back in relation to the drive by the restoring spring 525 until it contacts, via a second control curve traveler 526, a further control curve 525, which is attached to the second part 503b of the drive rotor 503. The further control curve 527 thus forms a retraction stop, by which the piercing element 5 is stopped at the end of the retraction phase R1. If the drive rotor 503 comes to a standstill at the end of the retraction phase R1, a defined position of the lancet holder 507 in relation to the reference element carrier 511 is thereby achieved, in which the piercing element 504 projects beyond the edge of the reference element 510 by the predefined residual puncturing depth. After termination of the collecting phase, the piercing element 505 is withdrawn completely from the skin by moving the first carriage 521 backwards by means of the electric motor 520.

The described puncturing system has the advantage that the reference element is only pressed against the skin for a short time, preferably less than 2 ms. In this manner, the depth of the piercing may be controlled, but with such a short contact pressure the viscoelastic properties of the skin do not cause a deterioration of the precise definition of the residual puncturing depth by a deformation of the skin.

The invention claimed is:

1. A microsampler puncturing system for collecting a body fluid sample from a body part, comprising:
   a sample collection unit having a piercing element, and
   a puncturing instrument having:
      a drive, wherein the sample collection unit is movable on a movement path in a piercing and retraction movement for piercing the piercing element into skin of the body part, creating a piercing wound and withdrawing the piercing element thereafter,
   a setting device configured to set a defined puncturing depth of the piercing wound, and
   a control device configured to control the piercing and retraction movement, the piercing and retraction movement including the following sequentially executed movement phases:

a forward phase, in which the piercing element is moved in a puncturing direction and pierced to the defined puncturing depth, a retraction phase, in which the piercing element is partially withdrawn by a retraction distance and is decelerated toward an end of the retraction phase, in such a manner that the piercing element projects into the skin to a residual puncturing depth, and a collecting phase, in which a body fluid sample is withdrawn by the sample collection unit, via the piercing element projecting into the skin and being stationary, such that the residual puncturing depth is constant, or moving opposite to the puncturing direction, wherein a mean value of the residual puncturing depth corresponds to the time integral of the residual puncturing depth from the beginning of the collecting phase to the end of the collecting phase divided by the duration of the collecting phase, the setting device is adapted to set the defined puncturing depth independently of the mean value of the residual puncturing depth and the setting device is adapted to set the mean value of the residual puncturing depth independently of the defined puncturing depth.

2. The puncturing system according claim 1, wherein the control device is adapted to control, as a further movement phase, a further retraction phase, in which the piercing element is accelerated again and withdrawn completely from the skin.

3. The puncturing system according to claim 1, wherein the puncturing instrument comprises a retraction stop, wherein the piercing element is stopped at the residual puncturing depth at the end of the retraction phase.

4. The puncturing system according to claim 3, wherein the retraction stop comprises a spring element, wherein an abutting element of the retraction stop is moved into a blockade position to stop the piercing element.

5. The puncturing system according to claim 1, further comprising a reference element which is adapted for contacting the skin surface to ensure a reproducible defined puncturing depth during piercing, the reference element being movable in relation to the piercing element and in relation to a device housing.

6. The puncturing system according to claim 5, wherein the piercing element is moved together with the reference element in the puncturing direction during at least a part of the forward phase, and the reference element is moved backward opposite to the puncturing direction during at least a part of the retraction phase.

7. The puncturing system according to claim 6, wherein the reference element is moved forward simultaneously with the piercing element toward the end of the forward phase by at most 5 mm.

8. The puncturing system according to claim 7, wherein the reference element rests in a rest position during a part of the forward phase and is accelerated toward the end of the forward phase in the puncturing direction starting from the rest position.

9. The puncturing system according to claim 6, wherein the part of the forward phase during which the reference element is moved together with the piercing element is at most 100 ms in duration.

10. The puncturing system according claim 5, further comprising a drive spring that is, during at least one part of the forward phase, coupled to the piercing element; the reference element being, during at least a part of the one part of the forward phase, coupled via a co-transport device to the piercing element and thus to the drive spring; the co-transport device comprising a first puncturing depth delimiting stop coupled to the piercing element and a second puncturing depth delimiting stop coupled to the reference element; and the puncturing depth delimiting stops abut against one another in such a manner that their relative distance in a longitudinal direction at a reversal point of the piercing movement defines a longitudinal position of the piercing element in relation to the reference element, thereby defining the defined puncturing depth.

11. The puncturing system according to claim 10, wherein the reference element is coupled via a bidirectionally acting co-transport device to the piercing element and the drive spring, the co-transport device comprising stops coupled to the piercing element and to the reference element, wherein the stops abutting against one another during at least a part of the retraction phase in such a manner that the position of the piercing element in relation to the reference element is thereby defined.

12. The puncturing system according to claim 1, wherein the retraction phase between the end of the forward phase and the start of the collecting phase is at most 2 seconds in duration.

13. The puncturing system according to claim 1, wherein the drive is a spring drive.

14. The puncturing system according to claim 13, wherein the spring drive has a drive rotor driven by a drive spring.

15. The puncturing system according to claim 1, wherein the control device comprises a curve controller having a control curve and a control curve traveler for traveling along the control curve.

16. The puncturing system according to claim 15, wherein the control curve comprises an active section along which the control curve traveler travels during the forward phase and the retraction phase, the active section having at least one boundary that is adjustable for setting at least one of the defined puncturing depth and the residual puncturing depth.

17. The puncturing system according to claim 16, wherein, with reference to the movement of the control curve traveler, an end of the active section of the control curve is adjustable for setting the residual puncturing depth.

18. The puncturing system according to claim 16, wherein, with reference to the movement of the control curve traveler, a start of the active section of the control curve is adjustable for setting the defined puncturing depth.

19. The puncturing system according to claim 15, wherein the control device comprises a second control curve and a second control curve traveler for traveling along the second control curve.

20. The puncturing system according to claim 19, wherein the control curve is provided on a first part of a drive rotor of the drive and the second control curve is provided on a second part of the drive rotor, a distance between the first part of the drive rotor and the second part of the drive rotor in the puncturing direction being adjustable by a setting device.

21. The puncturing system according to claim 19, wherein at least one of the control curve travelers is not guided during a part of the piercing and retraction movement by the respective control curve(s) of the at least one control curve traveler, the part of the piercing and retraction movement being adjustable by a setting device.

22. The puncturing system according to claim 1, wherein the control device comprises a pivot unit which is pivotable from a starting position into a final position, thereby causing the piercing and retraction movement of the piercing element, the final position being defined by an end stop which is adjustable to set the residual puncturing depth.

23. The puncturing system according to claim 22, wherein the pivot unit includes a parallelogram guide.

24. The puncturing system according to claim 22, wherein the pivot unit includes a toggle lever.

25. The puncturing system according to claim 22, wherein the starting position is defined by an adjustable starting stop.

\* \* \* \* \*